(12) United States Patent
Mohajer et al.

(10) Patent No.: US 7,135,870 B2
(45) Date of Patent: Nov. 14, 2006

(54) DEVICE FOR DETERMINING THE COMPOSITION OF A FLUID MIXTURE

(75) Inventors: Kim Mohajer, Houston, TX (US); Edward McChesney Browne, Houston, TX (US); Abbas Khajeh, Richmond, TX (US)

(73) Assignee: Kam Controls Incorporated, Houston, TX (US)

( * ) Notice: Subject to any disclaimer, the term of this patent is extended or adjusted under 35 U.S.C. 154(b) by 0 days.

(21) Appl. No.: 11/119,556

(22) Filed: May 2, 2005

(65) Prior Publication Data

US 2005/0264302 A1   Dec. 1, 2005

Related U.S. Application Data

(60) Provisional application No. 60/567,838, filed on May 4, 2004.

(51) Int. Cl.
*G01R 27/04* (2006.01)

(52) U.S. Cl. ........................ 324/639; 324/698
(58) Field of Classification Search ................ 324/639, 324/642, 643, 698
See application file for complete search history.

(56) References Cited

U.S. PATENT DOCUMENTS

| | | | |
|---|---|---|---|
| 4,112,744 A | 9/1978 | Tassano | 73/61.61 |
| 4,266,188 A | 5/1981 | Thompson | 324/649 |
| 4,646,070 A * | 2/1987 | Yasuhara et al. | 340/603 |
| 4,862,060 A | 8/1989 | Scott et al. | 324/639 |
| 4,996,490 A | 2/1991 | Scott et al. | 324/639 |
| 5,014,010 A | 5/1991 | Helms et al. | 324/640 |
| 5,025,222 A | 6/1991 | Scott et al. | 324/639 |
| 5,033,289 A | 7/1991 | Cox | 73/61.43 |
| 5,101,163 A | 3/1992 | Agar | 324/639 |
| 5,103,181 A | 4/1992 | Gaisford et al. | 324/637 |
| 5,132,903 A | 7/1992 | Sinclair | 73/61.44 |
| 5,272,444 A | 12/1993 | Cox | 324/698 |
| 5,400,651 A * | 3/1995 | Welch | 73/290 R |
| 5,503,004 A | 4/1996 | Agar | 73/61.44 |
| 5,596,150 A | 1/1997 | Arndt | 73/861.12 |
| 5,675,259 A | 10/1997 | Arndt et al. | 324/642 |
| 5,723,979 A * | 3/1998 | Mohr | 324/642 |
| 5,898,308 A * | 4/1999 | Champion | 324/643 |
| 5,966,017 A | 10/1999 | Scott et al. | 324/639 |
| 6,144,211 A * | 11/2000 | Mohr | 324/642 |
| 6,867,603 B1 * | 3/2005 | Nicholson et al. | 324/698 |
| 6,927,583 B1 * | 8/2005 | Vanzuilen et al. | 324/686 |

* cited by examiner

*Primary Examiner*—Walter Benson
(74) *Attorney, Agent, or Firm*—Elizabeth R. Hall

(57) ABSTRACT

A method and apparatus are disclosed for determining the concentration of individual components within a fluid mixture by determining the permittivity of the individual components. The method and apparatus use a reference sensor and at least one measurement sensor positioned inside the same sensor device that is immersed in the fluid mixture to be measured. Signals, such as radio frequency or microwave, are sequentially transmitted at multiple, known, constant frequencies to and reflected from both the reference and measurement sensor(s). Permittivities of the individual components are determined from these transmitted and reflected signals and information about the concentration of the individual fluids and other compounds within the fluid mixture and the density of the fluid mixture are produced. Repetitive sampling and processing of these signals allow determination and real-time monitoring of the concentration of individual components within a mixture of fluids. The present invention provides self-calibration, accurate frequency maintenance and self-selection of an operating frequency range.

49 Claims, 13 Drawing Sheets

DEVICE FOR DETERMINING THE COMPOSITION OF A FLUID MIXTURE

CROSS REFERENCE TO RELATED APPLICATIONS

This application claims priority to pending U.S. Patent Application Ser. No. 60/567,838 filed May 4, 2004 by inventors Kim Mohajer, Ed Browne and Abbas Khajeh and entitled "Device for Determining Composition of Fluid Mixture".

BACKGROUND OF THE INVENTION

1. Field of the Invention

The present invention relates in general to a method and apparatus for determining the concentration of components (such as water, oil, salt and sulfur) in a fluid mixture. More particularly, the present invention relates to a method and apparatus for determining the concentration of individual components within a mixture of fluids by utilizing the permittivity of the individual components when the permittivities of the different components are measurably distinct.

2. Description of the Related Art

Knowledge of accurate water content, salt content, sulfur content, and density of the hydrocarbon and chemicals for a fluid mixture is important for oilfield reservoir management, royalty allocation, buying and selling, corrosion management, refining, chemical processing, and aviation safety. An automated measuring device would be desirable for performing such determinations.

One possible means of measuring the ratio of fluids in a sample involves the use of radio frequency (RF) or microwave energy to determine the capacitance or permittivity of a fluid sample consisting of oil and water. Since these properties can be related to the ratio of water in oil, several devices based on this approach have been developed. However, several perturbing factors adversely influence currently available measurement means to yield highly erroneous data.

Water is an excellent solvent of salt and other contaminants found in petroleum based fluids. An unknown salt concentration typically gives rise to significant errors in the measurement of water concentration in a hydrocarbon fluid mixture. If the percentage of salt is known, then compensation for the salt content can be made. However, if the salt concentration varies over time, instrument error will be increased unless there is active compensation for the varying influence of the salt. Likewise, interactions between sulfur compounds and the water in a hydrocarbon fluid mixture will adversely influence the accuracy of the measurement of water concentration in the fluid mixture. Furthermore, the temperature and density variations of the fluid also influence the measurement of the water concentration. There is a present need for a simple, accurate, reliable, and stable means for determining the concentration of oil and other contaminants in a hydrocarbon fluid mixture, particularly given the major economic impact of incorrect measurements.

In most currently available microwave systems, a measurement is made of frequency changes in an oscillator circuit that are caused by impedance changes of the mixture as the concentrations of the components in the mixture change. Various components have different dielectric constants, which are proportionally related to the overall impedance of the mixture. Binary systems, such as water in oil, are relatively easy to measure. Increasing the number of components significantly, however, adds to the problem. Water is a solvent for many things, such as various salts that significantly affect the complex permittivity of the mixture.

The complex permittivity of many materials changes with the frequency used for the permittivity measurement. Thus, as the oscillator frequency is changed, the complex permittivity also changes and the resulting system of mathematical equations used to describe and solve for the component concentrations become increasingly non-linear. If, however, the permittivity measurements can be made at accurate and repeatable frequencies, the fluid system components could be determined from simple linear equations.

Newer microwave apparatus use multiple oscillators or voltage-controlled-oscillators (VCOs) to measure a wider range of water concentrations. As with any electronics, these oscillators are subject to drift due to the temperature of the ambient surroundings or from self-heating and aging of the components. It is difficult, or impossible, to separate drifts in the oscillator from actual impedance changes in the fluid medium; and, as explained previously, non-linear dielectric constants tend to magnify the measurement errors.

Some systems include a reference oscillator calibrated to provide a specific frequency for a known impedance, but the reference oscillator is subject to the same thermal and aging errors. In fact, component aging and thermal effects might have offsetting effects and move the reference frequency in the opposite direction from the measurement frequency. Thus, the reference and measurement oscillators require frequent calibration and recalibration.

Often measurements of hydrocarbon fluids (with admixed water and other contaminants) are made as the fluid is flowing from one location to another, such as into or out of a truck or ship, through a pipeline or from a wellhead. Thus, it is necessary to be able to measure the contaminants in the fluid as it is moving. As the fluid mixture moves through the measurement system, the relative concentrations of individual fluid components passing through the system will vary. Particularly in cases of laminar flow or irregular mixing, fluctuations in individual fluid components can change rapidly. Because the calculations of fluid concentrations assume stationarity (in a stochastic sense) or component fluid property constancy during the measurement time, it is important that the measurements be done such that an instantaneous "snapshot" of the fluid makeup is made. Ideally, several measurements would be made instantaneously, or at least fast enough so that the fluid's components could be considered constant during the period of measurement.

Various types of capacitance (radio frequency measurement), microwave (microwave energy measurement), and optical (spectrometer) apparatus have been used for measuring the concentration of one substance in another, particularly for measuring the water content in hydrocarbons.

Tassano in U.S. Pat. No. 4,112,744, Thompson in U.S. Pat. No. 4,266,188, and Scott et al. in U.S. Pat. No. 4,996,490 have described single frequency measuring devices. Tassano, in U.S. Pat. No. 4,112,744, discloses an apparatus for detecting water in oil that uses a capacitive probe immersed in a sample of pure oil similar to the oil in the fluid mixture under test. The apparatus alternatively connects a reference capacitor and the measuring probe capacitor to an electronic capacitance measuring circuit that produces an output signal indicating changes in the dielectric constant of the oil. In this system the reference capacitor will only compensate for the measuring circuit drift and aging, but not the pressure and temperature of the oil and water mixture. The single operating frequency of the unit is 50 kHz, rendering the unit incapable of dealing with variations in the measurement due to variations in salt and sulfur compounds.

Thompson in U.S. Pat. No. 4,266,188 discloses a method and apparatus for measuring a component, namely water, in a two-component flowing fluid mixture using a probe having three sets of sensor electrodes positioned in the mixture. One set of electrodes is placed into an elastic sack filled with water, the second set of electrodes is placed into an elastic sack filled with a pure oil similar to the type being measured, and the third set of electrodes are exposed to the fluid being measured. Each set of electrodes produces a signal representative of a measured electrical property of the liquid in which they are immersed, either resistivity or conductivity or alternatively capacitance or dielectric constant. Since any changes in temperature and pressure in the mixture being measured will affect the reading from all three sensors equally, the probe is considered self-adjusting so that the accuracy of the final measurement is relatively unaffected by these changes. Nevertheless, the measurement accuracy will be affected when there are changes in either oil composition or in water salinity of the actual mixture being measured. The operating frequency for the unit is not disclosed.

Scott et al. in U.S. Pat. No. 4,996,490 discloses an apparatus for measuring the concentration of one material, such as water, in another material, such as crude or refined oil, utilizing a microwave transmission line formed by a conduit for receiving the material and a center conductor sheathed with a dielectric covering. This covering operates to prevent short-circuiting the transmission path. An oscillator circuit is coupled to the transmission line and is driven by a free-running voltage controlled oscillator. A signal receiver monitors changes in frequency caused by impedance pulling of the oscillator due to the change in the dielectric constant of the mixture. Power transmitted to the fluid mixture and power reflected from the fluid are measured to determine whether an oil-in-water or water-in-oil emulsion is present and to verify the concentration of one fluid in the other for a particular single operating frequency. The operating frequency of this unit is not disclosed. The single frequency measurement of this device is unable to ascertain the effects of varying concentrations of salt or sulfur compounds in the fluid mixture.

Single frequency capacitance apparatuses have not been successful in measuring the water content of the hydrocarbon in high concentrations because salt, sulfur, density, and temperature adversely influence the capacitance reading.

One possible means of treating the problems described above for microwave or capacitance measuring devices involves the use of permittivity measurements at multiple frequencies, since such measurements permit inference of the salt or sulfur compound percentages in the fluid sample. This permits determination of the permittivity of the fluid mixture, which is a mathematically complex measurement in that it has both real and imaginary components, such as $A+B\times i$, where A is the real component and $B\times i$ is the imaginary component, with i being the square root of $-1$.

Fluid complex permittivity measurements for monitoring of fluid concentration are influenced by multiple important components, including the measuring cell or sensor, the measuring electronics, and the physical model for complex permittivity of the fluid mixture.

The patents discussed below propose solutions to the problem of determining individual components of fluid mixtures. Each of these patents discloses different technical means for measurement, yet each patent is based on the same flawed concept (i.e., if the fluids constituting the mixture are exclusively crude oil and water, then, because the permittivities of crude oil and water are known and divergent with frequency change, the permittivity of the mixture can be measured and an algebraic formula used to find the ratio of the mixture components).

Helms et al. in U.S. Pat. No. 5,014,010 discloses a dual frequency microwave water content monitor. Microwave oscillators provide two different frequencies of microwave energy to an antenna, which transmits the microwave energy into a petroleum stream and receives microwave energy reflected back from the stream. The microwave energy provided by the antenna also passes through the petroleum stream and is received by another antenna. Both signal phase shift and attenuation are measured. Two frequencies are used to resolve ambiguities in signal phase shift. Measured signal attenuation and phase shift are used to determine the type of emulsion measured (i.e., oil-continuous or water-continuous). The preferred operating frequencies of the disclosed apparatus are 10.119 GHz and 10.369 GHz, although the two frequencies selected should be substantially different.

Cox in U.S. Pat. No. 5,033,289 and U.S. Pat. No. 5,272,444 discloses a water percentage monitoring means and method in which the water content of a petroleum-containing stream is measured by comparing a probe signal to a reference signal. A probe is located in the pipeline and is connected to the reference signal through a series resistance. The signal from the oscillator side of the resistor is converted into two reference signals: one with zero phase shift and one with 90 degrees phase shift. These two reference signals are mixed with the signal on the probe side of the resistor, which changes as a function of the complex electrical impedance, primarily capacitive, of the fluid stream. The real part of the complex impedance is measured with the zero phase shifted reference signal. This is the resistance/conductivity of the fluid, while the imaginary part of the complex impedance is obtained by mixing the 90 degree phase shifted reference with the probe side of the resistor to measure the capacitance/permittivity of the fluid. The resistance/conductivity versus the capacitance/permittivity measurements provide enough information to derive a water content value in a true oil-based emulsion or water-based emulsion without further contaminants such as salt. The operating frequency range of the Cox invention is 10–200 MHz, with the preferred operating frequency at approximately 20 MHz.

Agar in U.S. Pat. No. 5,101,163 discloses a device for measuring the concentration of two admixed fluid substances through the transmission of electromagnetic waves. The device utilizes a transmission element for transmitting a signal and two receiving elements for receiving the signal and providing first and second output signals. The system utilizes a receiving device for receiving the first and second output signals and measuring the ratio and/or the phase difference of the powers received by each receiver. Since oil absorbs very little energy compared to water, the amount of power received in each antenna is a function of the water content and the distance from the transmitting antenna.

Gaisford et al. in U.S. Pat. No. 5,103,181 discloses a composition monitor and monitoring process using impedance measurements with radio frequency bridge techniques to parameterize the complex dielectric properties of the fluids. The method uses the pipe with the mixture of fluids as a waveguide in which two transmission channels are established. These transmission channels are used as arms of a Wheatstone bridge that is balanced using variable phase shift and attenuation units. The operating frequency of the disclosed apparatus is in the range of 50 MHz–3 GHz.

Sinclair in U.S. Pat. No. 5,132,903 discloses a method and apparatus for analyzing oil and water mixtures in a well borehole, where the sensor is formed by two coupled lines. Because the dielectric constant of the tested fluid affects the coupling coefficient between the two lines, measuring transmitted signal power allows the fluid properties to be evaluated and converted to water content. The practical operating frequency range for the device ranges from 200 MHz–5 GHz, with a preferred operating frequency of about 2.5 GHz.

Agar et al. in U.S. Pat. No. 5,503,004 discloses a method and apparatus for measuring the percentages of oil and water present in a mixture. By measuring the energy absorption properties of the oil/water mixture, the percentages of oil and water present in the oil/water mixture can be determined regardless of whether the oil or the water is in the continuous phase and regardless of what the relative proportions of water and oil are. Measuring the energy absorption properties of the oil/water mixtures allows the apparatus to determine whether the oil or the water is in the continuous phase so that the proper data curve is selected and the percentage of water present can then be determined. The specified operating frequency of the disclosed apparatus is 2.45 GHz, but the possibility of using two or more distinct frequencies to obtain more information about the fluid's components is mentioned.

Arndt et al. in U.S. Pat. No. 5,596,150 and U.S. Pat. No. 5,675,259 disclose a method and apparatus for making complex permittivity measurements of mixed fluids including the use of a capacitive probe. The impedance of the probe is determined in part by the complex dielectric constant of the fluids between the probe electrodes. The percentage of fluid component present in the flow stream is identified from the permittivity variations of the flow stream. The operating frequency of the disclosed apparatus is approximately 1 GHz.

Scott et al. in U.S. Pat. No. 5,966,017 discloses devices, methods and systems using load-pulled electronic monitoring. The patent primarily discusses various probe configurations and probe terminations as used to measure various chemical substances. It discloses various techniques for chemical absorption/desorption as applied to microwave detectors and some variations on load-pull electronics. The transmission line based probe does not necessarily have to end in an open connection. Termination of this transmission line can be accomplished in several alternate ways: a resistor, capacitor, inductor, short, or diode. Several different operating frequencies were mentioned for the disclosed apparatus include 200 MHz, 400 MHz, 600 MHz, and 1.2–1.3 GHz.

Spectrographic optical apparatuses represent a new approach and have been used successfully in limited applications. However, optical apparatuses have not proven effective for midrange water concentrations. This type of device also requires extensive periodic recalibration, and measurement errors increase as the optical sources and/or sensors become dirty, as is often the case in oilfield applications.

None of the apparatuses disclosed or currently available are able to self-calibrate, automatically select and switch the frequency range, find the optimum frequency, and/or make rapid multiple measurements to accurately measure oil and water mixture ratios, salt and sulfur content, as well as the density of the fluid mixture. There is an existing need for a means for accurately determining the content of oil, water, salt and sulfur in complex fluid mixtures. There is a further need for a means determining individual components in fluid mixtures that is self-calibrating.

SUMMARY OF THE INVENTION

A method and apparatus are disclosed for determining the concentration amounts of individual components of a fluid mixture. The method and apparatus immerse a sensor device into the fluid mixture where the sensor device has a reference sensor and at least one measurement sensor. Each sensor has an electrode and a transmission line from a signal source. The transmission lines are independently adjustable in length and are preferably the same length.

Identical exposure of the reference and measurement sensors to pressure and temperature of the fluid mixture is done to minimize anomalies. Multiple, approximately concurrent measurements are made by energized measurement sensor(s) of identified parameters at various predetermined frequencies. The reference sensor is activated to detect anomalies in the measured parameters. Compensation factors are applied to the measured parameters for the detected anomalies. Permittivities of the individual components are then calculated, based on the compensated parameters. The calculated permittivities at the selected measurement frequencies are then used to determine the concentration amounts of individual components of the fluid mixture.

Another aspect of the present invention is a sensor device for determining the concentration of fluid components within a fluid mixture comprising: a) a microcontroller; b) a sensor probe including (i) a probe body having at least two fluid opening for allowing a fluid mixture to flow through the probe body, (ii) a measurement sensor within the probe body, the measurement sensor having a measurement electrode in communication with the fluid mixture and a measurement transmission line, and (iii) a reference sensor within the probe body, the reference sensor having a reference electrode in communication with a reference transmission line, wherein a portion of the reference electrode is covered by a reference isolator; and c) an electronics instrument package in communication with the microcontroller, the electronics instrument package having a signal generating/receiving unit in communication with the measurement transmission line and the reference transmission line, wherein the signal/receiving unit reciprocably activates the measurement electrode and the reference electrode to measure a parameter of the fluid mixture at a predetermined frequency, wherein the microcontroller calculates a permittivity of a component of the fluid mixture based on multiple measurements of the measured parameter by the reference sensor and the measurement sensor; whereby the microcontroller determines the concentration of the component in the fluid mixture using the calculated permittivity.

BRIEF DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

Figure 1:
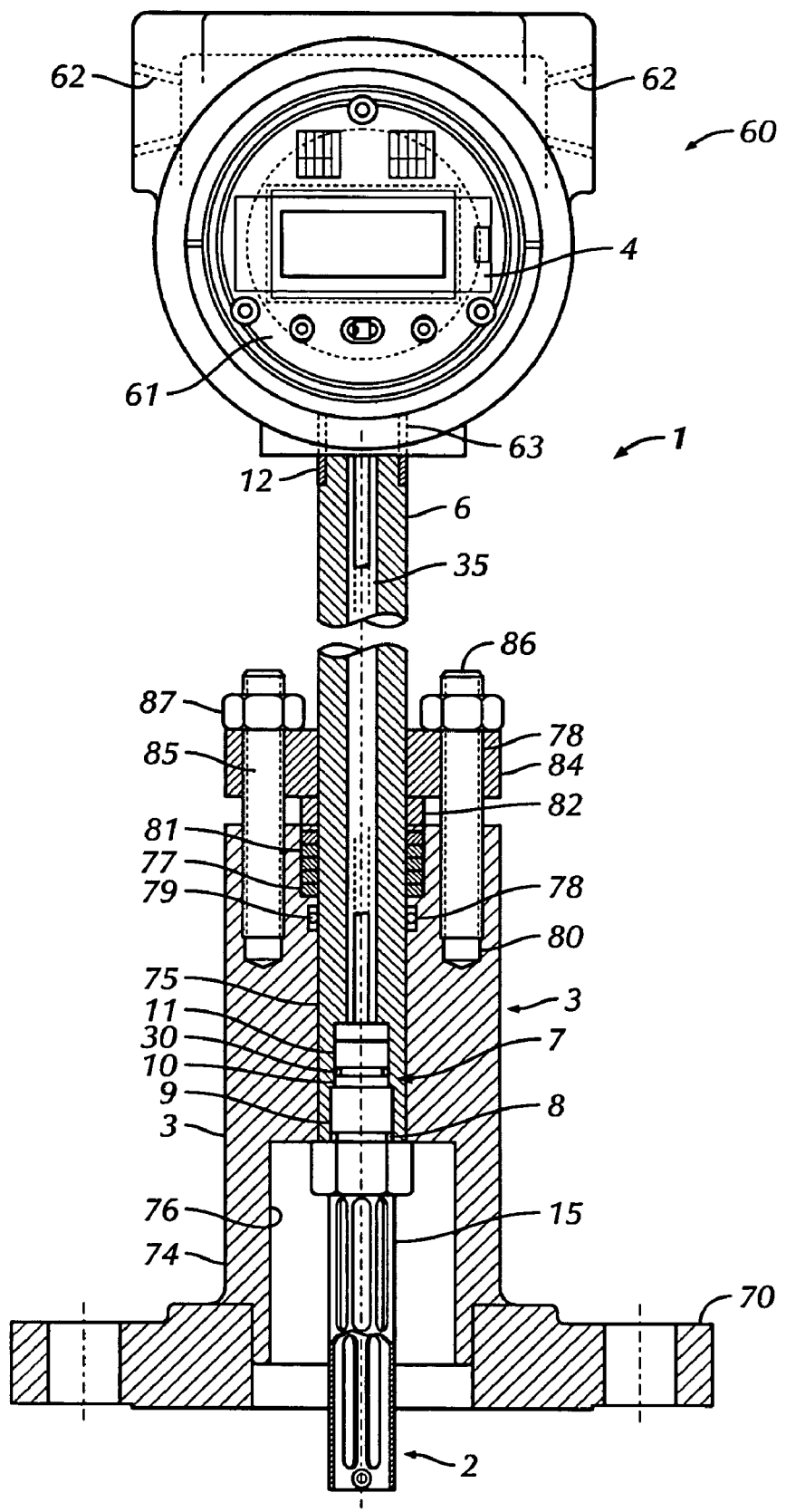
FIG. 1 is a partial longitudinal cross-sectional view of a first embodiment of the invention illustrating the sensor device in a flange mount configuration.

The present invention provides a method and apparatus for determining the concentration of individual components within a mixture of fluids by measuring the complex permittivity of the mixture of fluids. The measurement of complex permittivity requires that the probe of the sensor device be immersed in the fluid mixture and be operated at more than one frequency so that both the real and imaginary parts of complex permittivity can be determined and processed.

As long as each individual component within a mixture of fluids can be identified by its individual complex permittivity, the present invention can distinguish an individual fluid within a mixture of fluids and can evaluate the concentration of individual fluid components within the mixture of fluids.

Referring now to the drawings, it is pointed out that like reference characters designate like or similar parts throughout the drawings. The Figures, or drawings, are not intended to be to scale. For example, purely for the sake of greater clarity in the drawings, wall thickness and spacing are not dimensioned as they actually exist in the assembled embodiment.

Figure 4:
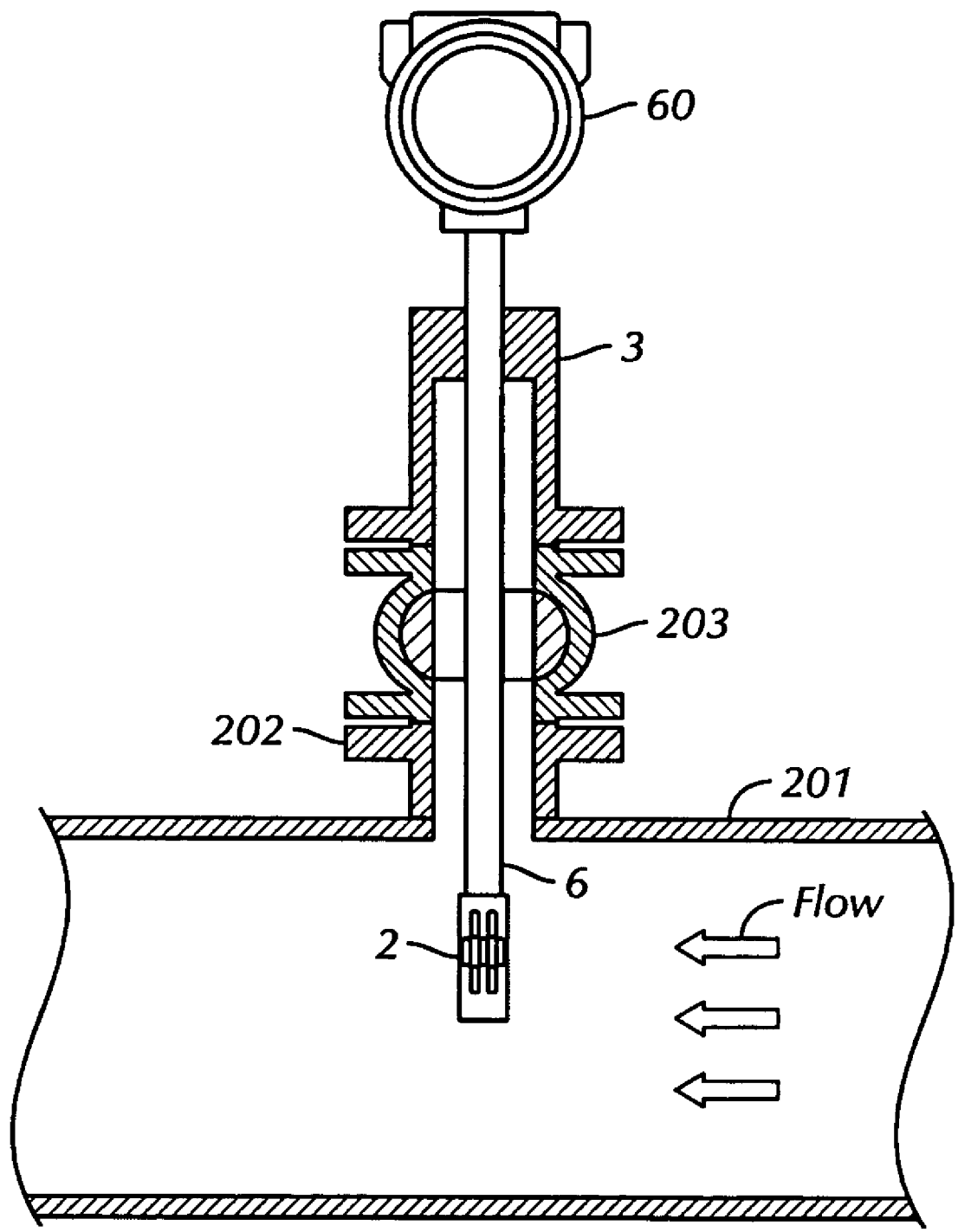
FIG. 4 is a partial cross-sectional view taken on the longitudinal mid-plane of symmetry of a pipeline showing the single probe configuration of the sensor device of FIG. 1 installed.
Figure 5:
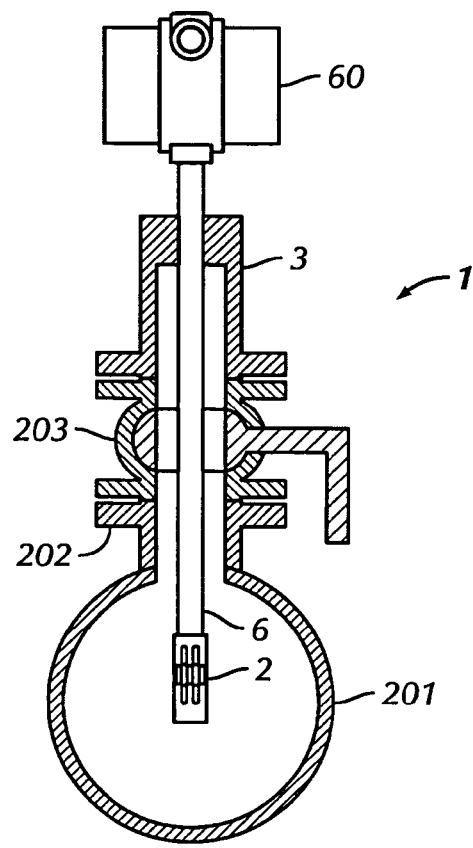
FIG. 5 is a partial transverse cross-sectional view of the installed sensor device shown in FIG. 4.

The first embodiment of a sensor device 1 of the present invention is shown in FIGS. 1, 4 and 5. The sensor device 1 is configured for flange mounting on a fluid conduit (such as a pipeline 201 shown in FIGS. 4–5) provided with a co-mating flange. Typically, a probe 2 of the sensor device 1 is radially inserted into a flow stream confined within a circular tubular conduit, such as a tank or pipeline 201.

The flow conduit is provided with a radial circular port either by having a welded mounting flange preinstalled with the port during fabrication or by being hot-tapped in service with a conventional hot-tap fitting and machine used to produce a port. In the latter case, the mounting flange is mounted on the outer end of the hot tap fitting or, alternatively, on a valve on the outboard end of the hot tap fitting. An example of a suitable hot tap fitting and hot tap machine would be the IPSCO Flostop II system, provided by the International Piping Services Company, Broadview Ill. 60153. The materials of construction of the sensor device 1 are typically 300 series stainless steel or another corrosion resistant alloy suitable for the service conditions of the device.

The first embodiment of the sensor device 1 consists of the probe 2, a probe mounting support 3 and an electronics instrumentation package 4. Probe 2 consists of a round tubular shaft 6, a sensor head 15, a seal assembly 40 and a probe lead wire 35. Shaft 6 has a smooth external surface of constant diameter suitable for sealingly mating with O-rings or other seals. At the lower end of shaft 6 is a recess 7 having, in order from its outer or lower end, a female recess groove 8 for the O-ring of a straight-thread/O-ring connection, a female threaded first counterbore 9, a conical transition shoulder 10 and a second counterbore 11. The upper end of shaft 6 is provided with a male pipe thread 12 by which the probe 2 is attached to the electronics instrumentation package 4.

Figure 2:
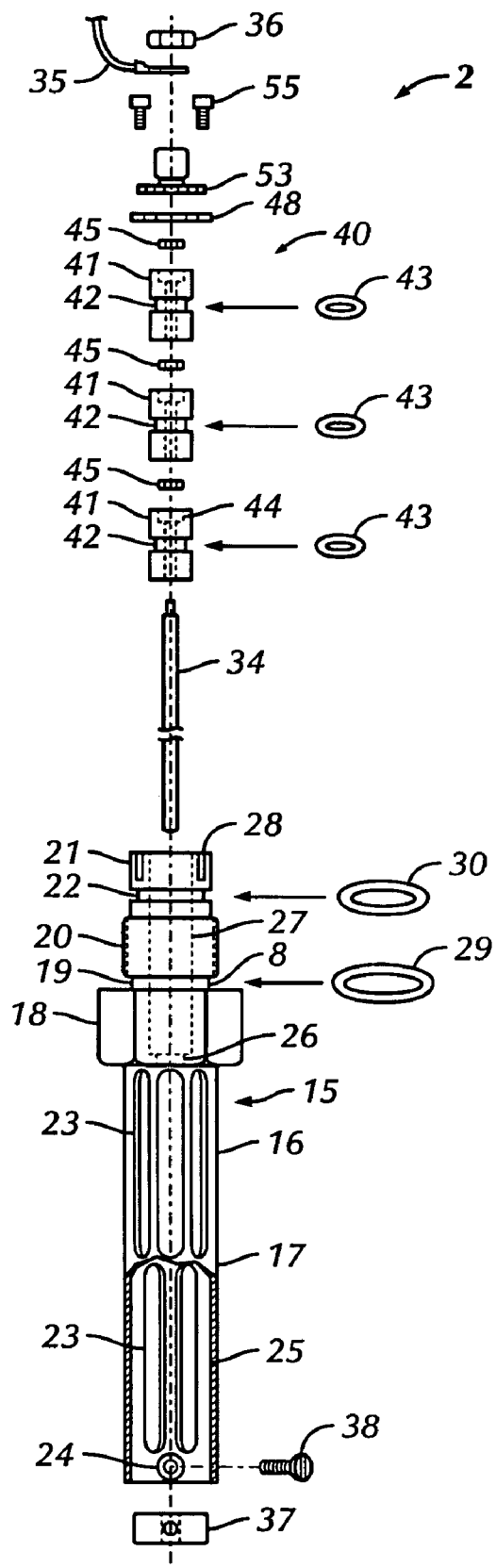
FIG. 2 shows an exploded view of the sensor device having a single probe configuration as shown in FIG. 1.

As seen in FIG. 2, sensor head 15 for probe 2 consists of a hollow body 16, a probe rod 34, an end cap 37 and end cap retainer screws 38. Body 16 has on its exterior, in order of position from its lower end, a thin walled shield 17, an integrally attached hex head 18, a male straight-thread/O-ring groove 19, a male thread 20 engageable with the female threaded first counterbore 9 of shaft 6 and a cylindrical segment 21 which has a male O-ring groove 22 positioned approximately in its middle. The point-to-point diameter of hex head 18 is somewhat larger than the outer diameter of shaft 6 of probe 2.

The shield 17 is typically on the order of 3 to 6 inches long with an outer diameter of 0.75 to 1.00 inch and an approximately 0.040-inch wall. Shield 17 has a series of multiple narrow longitudinally extending slots 23 cut through its wall around its circumference to admit the fluid to be sampled in the interior of the shield 17. Adjacent the lower end of shield 17 and in the same plane transverse to the body axis are multiple angularly equispaced and countersunk radial holes 24. From the lower end of body 16, the interior configuration consists of the bore 25 of the shield 17 which extends to hex head 18, a short reduced bore section, a transverse transition shoulder 26 and a counterbore 27 which extends to the upper end of the body 16.

The upper transverse face of body 16 is provided with a bolt circle of angularly equispaced multiple threaded holes 28. O-rings 29 and 30 are positioned in male O-ring grooves 19 and 22, respectively. Hex head 18 can be engaged with a wrench to threadedly engage male thread 20 into the female threaded first counterbore 9 of shaft 6, causing O-ring 29 to seal with groove 8 and O-ring 30 to seal with the second counterbore 11 of shaft 6.

Probe rod 34 is cylindrical with a diameter of approximately 0.08 to 0.14 inches and a length approximately 1 inch longer than that of body 16. The upper end of probe rod 34 is provided with a male thread that serves as an electrical terminal to which the probe lead wire 35 can be connected with a hex nut 36. Probe lead wire 35 extends through the bore of shaft 6 into the electronics instrumentation package 4 (FIG. 1). Probe rod 34 is positioned centrally within body 16 and extends from the lower end of the shield 17 through the body 16 to project past its upper end.

End cap 37 (FIG. 2) is a thin circular disk which has its outer diameter sized to be a close fit to the inner bore 25 of shield 17 and is provided with a central axial blind hole on its upper side which is a close fit to the diameter of probe rod 34. End cap 37 has multiple angularly equispaced radial tapped holes at its mid length corresponding to the holes 24 in the lower end of the shield 17. Flathead end cap retainer screws 38 are extended through holes 24 in the shield 17 to engage the threads of the radial holes of end cap 37 so that it is retained within the shield 17. At the same time, end cap 37 serves to centralize and electrically isolate probe rod 34 from the body 16 in the region of shield 17.

Seal assembly 40 (FIG. 2) consists of a set of multiple identical cylindrical insulator rings 41 made of a nonconductive plastic compound and which have external O-ring grooves 42 for mounting O-rings 43 at their mid-height. The axial length of the set of insulator rings 41 is slightly longer than the length of the second counterbore 27 of body 16. Each insulator ring 41 has an axial hole which closely fits to the outer cylindrical surface of the probe rod 34 and, on the upper end of each insulator ring 41, an O-ring face seal groove 44 which mounts O-ring 45. The outer diameter of the insulator rings 41 fits closely within counterbore 27 of body 16 so that O-rings 43 seal between the body 16 and the insulator rings 41.

A circular retainer disk 48 having an outer diameter approximately equal to that of the upper cylindrical segment 21 of body 16 is positioned above and with the uppermost of the insulator rings 41. Disk 48 is provided with a central hole which is sufficiently large to readily clear probe rod 34, but is small enough to engage the O-ring 45 of the upper insulator ring 41 so that the O-ring 45 can be squeezed between disk 48, probe rod 34 and its insulator ring 41 to seal therebetween. A bolt hole circle is provided in disk 48 corresponding to the holes 28 on the upper transverse face of body 16.

Positioned above and with disk 48 is straight jack flange 53, which consists of an approximately square flange plate and a concentric cylindrical projection on its upper side. An axial through hole with sufficient diameter to clear probe rod 34 extends through flange 53. Flange 53 has a bolt circle corresponding to that of disk 48 and holes 28 of the body 16.

Multiple clamp screws 55 are mounted in the bolt circles of flange 53 and disk 48 and are engaged in the threaded holes 28 of body 16 in order to clamp flange 53 against disk 48 which is in turn clamped against the set of insulator rings 41 and the transverse shoulder 26 of body 16. This clamping causes all of the O-rings 45 to seal between their respective insulator rings 41 and the probe rod 34 and, additionally, to clamp probe rod 34 against axial movement. Because the O-rings 45 and the insulator rings 41 are nonconductive and centralize the probe rod 34, the probe rod 34 is electrically insulated from body 16 and shaft 6.

Electronics instrumentation package 4 (FIG. 1) is housed within an instrument enclosure 60 (preferably explosion-proof) having a glass window on a cover 61. A typical enclosure 60 would be the Killark Electric Manufacturing Company Model HBK with a Model HKGL lens cover 61. The enclosure 60 is sealed to its cover 61 by an O-ring (not shown) and is provided with female pipe threaded outlets 62 for power and communication wiring and a female pipe threaded outlet 63 on its lower side for interconnection with the male pipe thread 12 of shaft 6.

The probe lead wire 35 enters the enclosure 60 through outlet 63. The body 16 of the probe 2 is electrically connected to shaft 6, which is in turn electrically connected to the body of enclosure 60. The electronic circuitry of the sensor device 1 is housed as a part of the electronics instrumentation package 4 and is positioned within enclosure 60 and cover 61.

Probe mounting support 3 consists of a flange 70, a seal housing 74, packing rings 81, a seal bushing 82, a collar 84 and seal activating hex nuts 87 mounted on threaded studs 86. The shaft 6 of probe 2 is deployed within probe mounting support 3.

Flange 70 typically is a standard steel or stainless steel ANSI 3-inch 150-pound flat face flange having multiple bolt holes in an angularly equispaced bolt circle. Flange 70 is provided with a central straight bore. Seal housing 74 has a generally cylindrical form with an outer diameter larger than that of the bore of flange 70 and with its external lower end having a reduced diameter that closely fits into the bore of flange 70. The transition between the outer diameter and the reduced external lower end of seal housing 74 is a transverse shoulder. The reduced diameter external lower end of housing 74 is inserted into the bore of flange 70 until the transverse shoulder abuts the flange 70 and the two pieces are welded together at both their external and internal interfaces.

Seal housing 74 has a central throughbore 75 with a large diameter counterbore 76 at its lower end extending approximately 40% of the length of the housing 74. This counterbore 76 is substantially larger than the outer diameter of shaft 6 and sensor head 15. Throughbore 75 is a close fit to the outer diameter of shaft 6 of probe support 3. At its upper end, throughbore 75 has an upper counterbore 77 which is approximately 0.25 inch to 0.50 inch larger in diameter than throughbore 75. The inner end of upper counterbore 77 is transverse to the seal housing axis.

Adjacent to and below upper counterbore 77 is a female O-ring groove 78 which contains an O-ring 79. The upper transverse end of seal housing 74 has a drilled and tapped equispaced bolt circle 80. Multiple packing rings 81 of conventional compressible packing material appropriate to the fluid and temperature conditions for the usage of the sensor device 1 are axially arrayed within the upper counterbore 77 and abutted against the transverse shoulder of that counterbore 77. Bushing 82 is an annular right circular cylindrical ring having its inner diameter a close fit to the shaft 6 of the probe 2 and its outer diameter a close fit to the upper counterbore 77 of seal housing 74. Bushing 82 abuts the upper end of the axial array of packing rings 81.

Collar 84 is an annular ring with a bore that has a slip fit over shaft 6 of the probe 2 and which has an outer diameter approximately equal to that of seal housing 74. Collar 84 abuts bushing 82 on its upper side. Collar 84 has a bolt hole clearance hole circle 85 corresponding to the bolt circle 80 on the upper end of seal housing 74.

Multiple threaded studs 86 and seal activating hex nuts 87 bearing on the upper side of collar 84 and deployed in bolt circles 85 and 80 can be tightened to urge bushing 82 against the array of packing rings 81 so that the packing rings 81 are axially compressed and will seal between shaft 6 of the probe 2 and seal housing 74. Additionally, when the packing rings 81 are compressed to seal against shaft 6, their friction against shaft 6 is sufficient that shaft 6 is unable to move axially in response to pressure forces.

Figure 3:
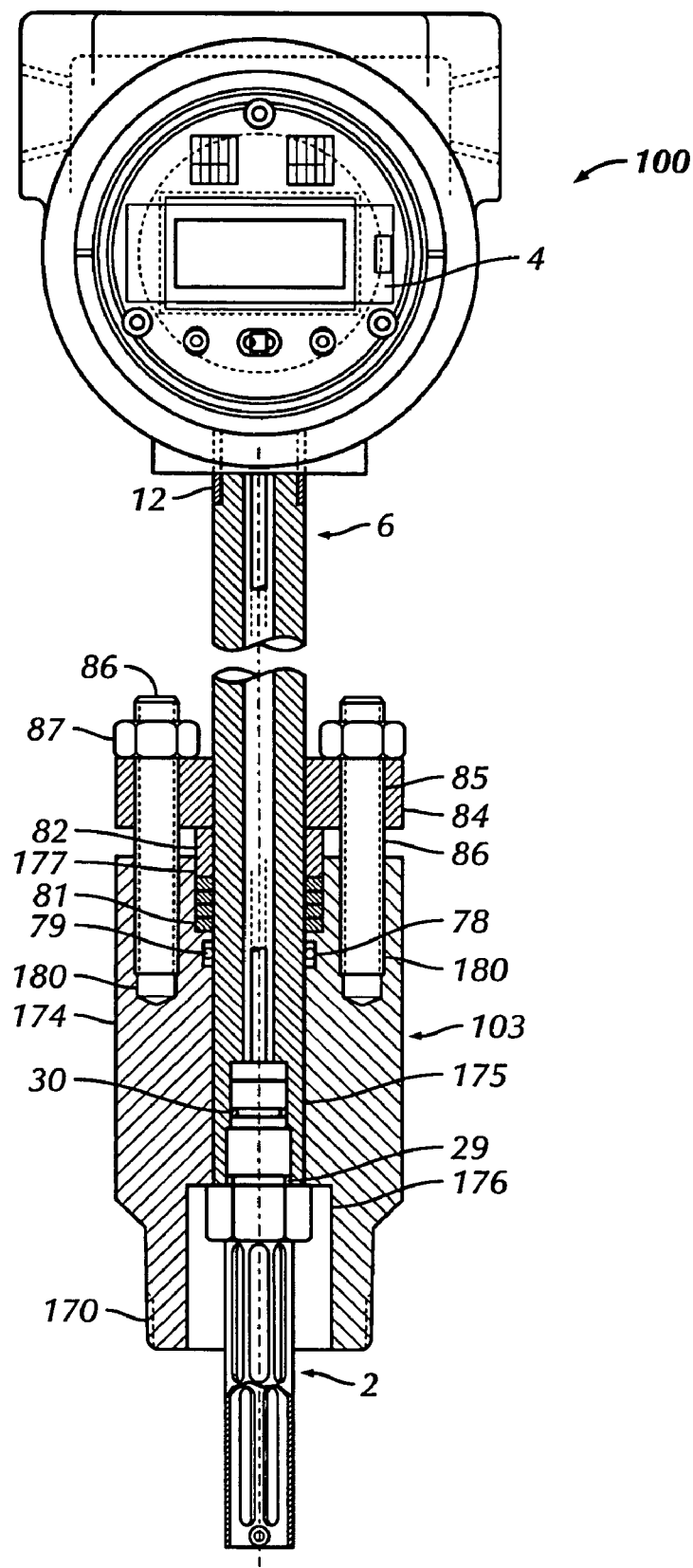
FIG. 3 shows a partial longitudinal cross-sectional view of a second embodiment of the invention, wherein the sensor device is provided with a screw-in body configuration.

The second embodiment 100 of the present invention, as shown in FIG. 3, differs from the first embodiment 1 only in the details of probe mounting support 103. Whereas the first embodiment 1 utilized a seal housing 74 welded to a flange 70 to effect mounting to the fluid conduit (FIGS. 1–2), the second embodiment 100 utilizes a probe mounting support 103 which has a male pipe thread 170 on the lower end of a seal housing 174 to connect to the fluid conduit. In all other details, the two embodiments 1 and 100 are essentially the same. Accordingly, only the probe mounting support 103 will be described for the second embodiment.

Probe mounting support 103 consists of seal housing 174, packing rings 81, seal bushing 82, collar 84 and seal activating hex nuts 87 engaged on threaded studs 86. The shaft 6 of probe 2 is deployedly within probe mounting support 103.

Seal housing 174 has a generally cylindrical form with an outer diameter of approximately 2.875 to 4 inches and with male pipe thread 170 at its lower end. Seal housing 174 has a central throughbore 175 with a large diameter counterbore 176 at its lower end extending approximately 40% of the length of the housing 174. This counterbore 176 is substantially larger than the outer diameter of shaft 6 and sensor head 15. Throughbore 175 is a close fit to the outer diameter of shaft 6 of probe support 2. At its upper end, throughbore 175 has an upper counterbore 177 which is approximately 0.25 inch to 0.50 inch larger in diameter than throughbore 175. The inner end of upper counterbore 177 is transverse to the seal housing axis. Adjacent to and below upper counterbore 177 is a female O-ring groove 78 which contains O-ring 79. The upper transverse end of seal housing 174 has a drilled and tapped equispaced bolt circle 180.

Multiple packing rings 81 of conventional compressible packing material appropriate to the fluid and temperature conditions for the usage of the sensor device 100 are axially arrayed within the upper counterbore 177 and abutted against the transverse shoulder of that counterbore 177. Bushing 82 is an annular ring having its inner diameter a close fit to the shaft 6 of the probe 2 and its outer diameter a close fit to the upper counterbore 177 of seal housing 74. Bushing 82 abuts the upper end of the axial array of packing rings 81.

Collar 84 is an annular ring with a bore which has a slip fit over shaft 6 of the probe 2 and which has an outer diameter approximately equal to that of seal housing 174. Collar 84 abuts bushing 82 on its upper side. Collar 84 has bolt hole circle 85 corresponding to the bolt circle 180 on the upper end of seal housing 174. Multiple seal activating hex nuts 87 engaged with threaded studs 86 bearing on the upper side of collar 84 and deployed in bolt circles 85 and 180 can be tightened to urge bushing 82 against the array of packing rings 81 so that the packing rings 81 are axially compressed and will seal between shaft 6 of the probe 2 and seal housing 174.

The sensor device 1 of the present invention is shown radially inserted and mounted in a tee connection in a pipeline 201 in FIGS. 4 and 5. The pipeline 201 contains a flowing mixture of fluids supplied by a well, a tank, or any other container (not shown). In this preferred embodiment, the sensor device 1 is installed into pipeline 201 through a Weldolet fitting 202 welded to the pipeline 201 and has a ball separation valve 203 mounted thereon so that the pipeline 201 can still be operated when the sensor device 1 is extracted from the pipeline 201. The sensor device 1 is mounted by its probe mounting support 3 to the external flange of the valve 203. The probe mounting support 3 provides mechanical stability to the sensor device 1 while inserted into the pipeline 201, as well as sealing sensor shaft 6 against fluid leakage past the exterior of the shaft 6.

Figure 6:
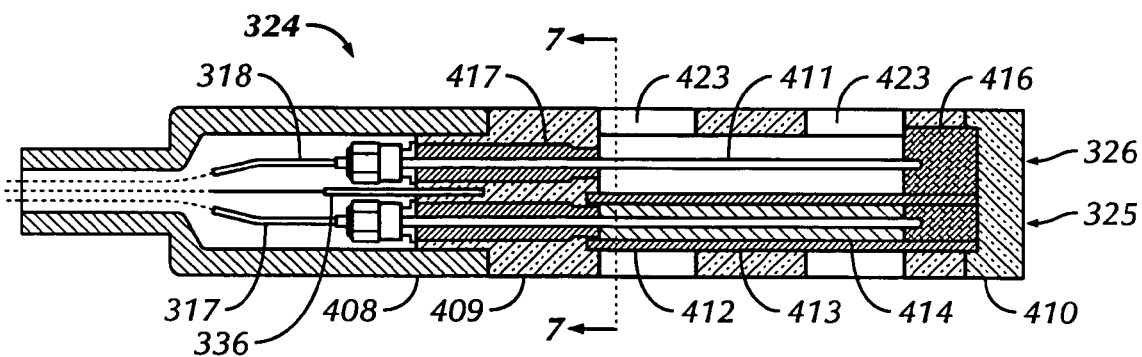
FIG. 6 is a longitudinal cross-sectional view of a dual-electrode configuration of the first embodiment having both reference and measurement sensors.
Figure 7:
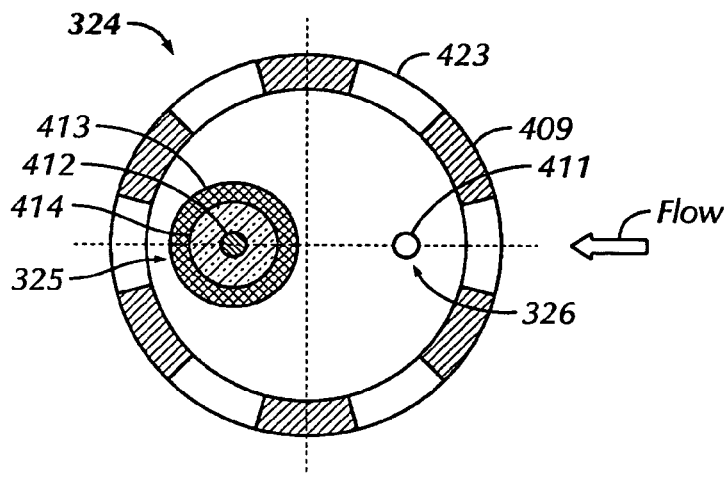
FIG. 7 is a transverse cross-sectional view of the dual-electrode configuration of the first embodiment taken along the line 7—7 of FIG. 6.

A dual-sensor probe 324 of the first embodiment, shown in FIGS. 6 and 7, consists of a top housing 408 with shaft connection, a cylindrical sensor body 409, an end cover 410, a measurement sensor electrode 411, a shrouded reference sensor electrode 412 and a reference sensor cylindrical jacket 413 isolated from reference sensor electrode 412 by a reference sensor shroud or isolator 414.

Measurement sensor electrode 411 is exposed to the mixture of fluids (not shown), which are transported to the electrode 411 through perforation slots 423 in the cylindrical wall of the sensor body 409. As shown in FIG. 6, an end isolator 416 supports the tips of measurement sensor electrode 411 and reference sensor electrode 412. Signals, such as radio frequency or microwave, are communicated to measurement sensor electrode 411 and reference sensor electrode 412 through identical feeders 417 that are connected to a measurement sensor line 318 and a reference sensor line 317, respectively. A reference temperature detector (RTD) 336 is imbedded in the sensor body 409 to monitor the temperature of the fluid mixture.

Figure 8:
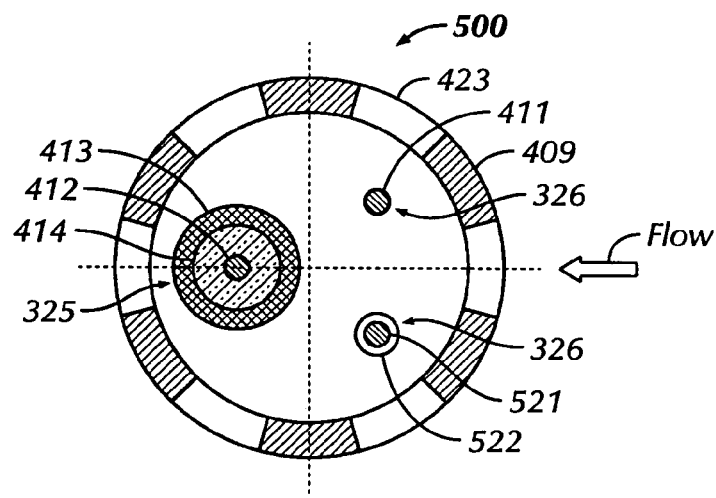
FIG. 8 is a transverse cross-sectional view of a triple-electrode configuration of the first embodiment having one reference electrode and two measurement electrodes.

The triple-electrode configured probe 500, shown in FIG. 8, is similar to the probe 324 shown in FIGS. 6 and 7, except that probe 500 has a second measurement sensor electrode 521 covered with a measurement sensor electrode shroud or isolator 522.

Figure 9:
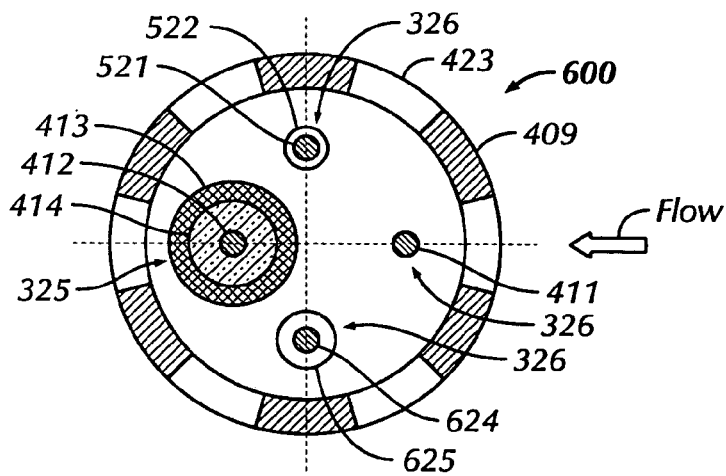
FIG. 9 is a transverse cross-sectional view of a quadruple-electrode configuration of the first embodiment having one reference electrode and three measurement electrodes.

A quadruple-sensor probe 600, shown in FIG. 9 in a cross-sectional frontal view, is similar to triple-electrode probe 500 but has a third measurement sensor electrode 624. The third measurement sensor electrode 524 is covered with a measurement sensor electrode isolator 625, which has a different wall thickness than the measurement electrode isolator 522. Sensors with multiple electrodes with isolating shrouds or isolators of various wall thicknesses can be independently selected based upon, for example, the fluid to be measured. This allows the range of fluid mixtures that the sensor device can measure to be extended without having to replace the sensor. Similarly, the determination to change sensors could be made by the instrument itself based upon impedance measurements so that it always operates in an optimum range.

Figure 10:
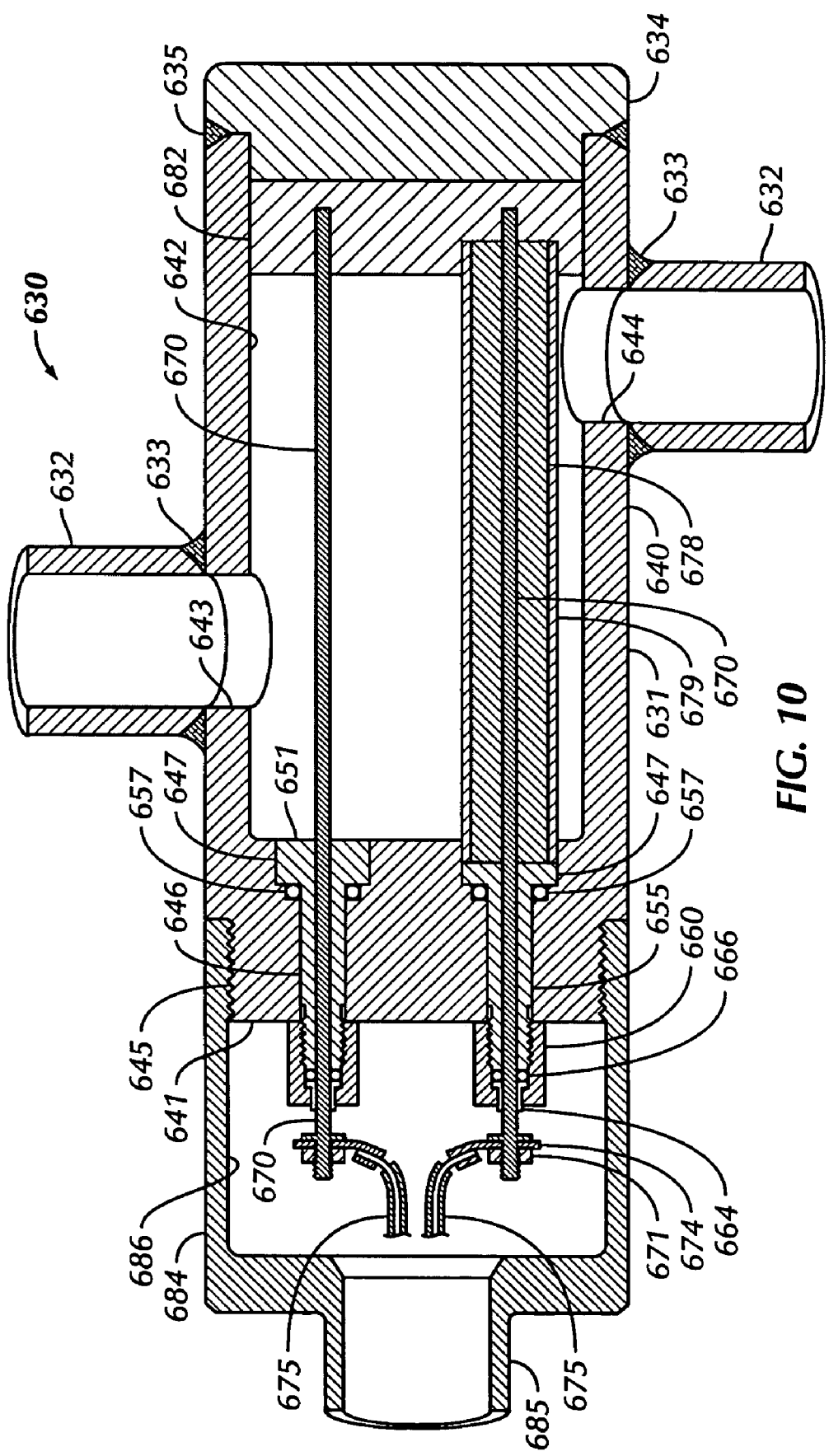
FIG. 10 is a longitudinal cross-sectional view of a third embodiment of the sensor device of the present invention, wherein the housing for the electrodes also serves as an offset flow path.

Referring to FIG. 10, a third embodiment 630 of the sensor device is shown in a longitudinal cross-sectional view. This particular embodiment is shown with one measurement electrode and one reference electrode but could be built with a multiplicity of electrodes in a manner similar to the construction of the multi-electrode probes 324, 500 and 600. This third sensor device embodiment 630 is arranged so that it can be connected into the flow line (not shown) by either a weld or thread connection.

A pressure containing body assembly 631, which houses sensor electrode rods 670, consists of a housing 640, two non-concentric radially positioned tube nipples 632 attached to housing 640 by welds 633 and an end cap 634 attached to a first end of housing 640 by a girth weld 635. The tube nipples 632 are right circular concentric tubular sections coped on a first end to conform to the cylindrical outer surface of the housing 640 and provided on their second ends (not shown) with either a welded connection or a male thread for a threaded connection. Circumferential welds 633 are used to provide a pressure retaining structural connection of the nipples 632 to the exterior of housing 640.

End cap 634 is a right circular cylindrical metallic disk having a chamfer on its outer side and an intermediate transverse shoulder with a reduced diameter cylindrical inner end which is a close fit to a concentric inner bore 642 of the housing 640. End cap 634 has a weld preparation bevel located at the intersection of its intermediate transverse shoulder and the larger diameter of the disk to accommodate its weld 635 to the housing 640.

Housing 640 is a right cylindrical metallic tube with a transverse bulkhead 641 and concentric inner bore 642 at its first end, and an external weld preparation groove at its second end. Circular wall penetrations 643 and 644 are aligned concentrically with the tube nipples 632. The axial positioning of the penetrations 643 and 644 is such that the interior volume enclosed by the bore 642 and the end cap 634 is well swept by flow entering one tube nipple 632 and exiting the other nipple 632. At its first end, housing 640 has an external thread 645 that is joined to the exterior of the housing 640 by a transverse shoulder. Two identical holes 646 penetrate the bulkhead 641 and are diametrically positioned and equispaced from the axis of symmetry of housing 640. Each hole 646 has, from its interior end, a counterbore 647, an interior transverse shoulder, an O-ring groove of the type used in straight thread O-ring sealed connections and a reduced diameter throughbore. An O-ring 657 is mounted in each of the O-ring grooves of the holes 646.

A first electrically insulating electrode holder 651 is inserted in the upper of the two holes 646 shown in FIG. 10. First electrode holder 651 is a concentric body composed of right circular cylindrical tubular segments. First electrode holder 651 has an elongated cylindrical main body with a male thread at its first end, an upset head joined to the main body by a transverse shoulder at its second end and a constant diameter throughbore. The transverse shoulder of electrode holder 651 abuts both the shoulder of the hole 646 and the O-ring 657 so that sealing between the holder 651 and the housing 640 is affected. The main body of electrode holder 651 is a close fit to the main bore of hole 646 and the upset head is a close fit to the counterbore 647. The length of the upset head of electrode holder 651 is equal to the depth of counterbore 647 and the threaded portion of the holder 651 extends beyond the first end of the housing 640. A second electrode holder 655 is identical to first electrode holder 651 except for its upset head length being approximately half of the length of that of the first holder 651.

A metallic tubular nut 660 is screwed onto the external thread of each of the electrode holders 651 and 655. Nut 660 has a regular hexagonal prismatic exterior, a transverse bulkhead with a central circular hole at one end and a female thread at the other end. The female thread is co-mateable with the male thread of either electrode holder 651 or 655, while the inner diameter of the hole in nut 660 is somewhat larger than the through hole in either of the electrode holders 651 and 655. A flanged tubular sleeve 664 of electrically insulating material has its flange abutting the inner side of the bulkhead of each nut 660 and its tubular shank extending through the central circular hole in the bulkhead. The bore of sleeve 664 is the same as that of either of the electrode holders 651 or 655. An O-ring 666 is concentrically positioned between each sleeve 664 and its corresponding electrode holder 651 or 655 so that it is compressed by its nut 660 when the nut 660 is tightened against the bulkhead 641 at the first end of housing 640. The lengths of the nuts 660 and the electrode holders 651 and 655 are chosen so that, when electrode rod 670 is inserted through electrode holder 651 or 655 and a nut 660, the electrode holder 651 or 655 will be firmly secured in the hole 646 of housing 640 while the O-ring 666 is sufficiently compressed to seat between the electrode rod 670 and the transverse first end of the electrode holder 651 or 655.

In this embodiment 630, identical electrode rods 670 are used. Each electrode rod 670 is an elongated right circular cylinder made of conductive metal and having at its connector end a male thread engageable by a hex nut 671 and an intermediate transverse flange adjacent the thread. As an alternative, the flange can be omitted and replaced by a second hex nut 671. Each electrode rod 670 is inserted through the center hole in installed electrode holder 651 or 655 and its nut 660 tightened so that flow past the electrode holder 651 or 655 is stopped by its O-ring 657 and flow past the electrode rod 670 is stopped by its O-ring 666. In this manner, each of the electrode rods 670 is caused to extend into the pressure containing body assembly 631 of the sensor device 630. A crimp-on ring wire terminal 674 with an attached wire 675 is clamped to the threaded end of each electrode rod 670 by a nut 671 to effect electrical connection between the rod 670 and the system electronics (not shown).

An inner thick-walled elongate right-circular cylindrical tube 678 of dielectric insulative material and an outer thin-walled conductive metallic right-circular cylindrical tube 679 which is a close slip fit over tube 678 and of the same length are installed concentrically over the lower of the two conductor rods 670 shown in FIG. 10. The bore through tube 678 is a close slip fit to the elongate portion of its conductor rod 670. A first end of the outer tube 679 is closely supported in the counterbore 647 of the lower hole 646 in the housing 640, while the other, second end is supported in a support disk 682 located in the righthand end of the body assembly 631, as shown in FIG. 10.

Support disk 682, located adjacent to the end cap 634, is a nonconductive right circular cylindrical disk having a close fit to the bore 642 of the housing 640. The interior transverse face of support disk 682 has two blind holes parallel to its axis in positions with the axes of the holes 646 in the housing 640. The upper hole is a close fit to the upper electrode rod 670 and serves as a support for the righthand tip of that rod 670. The lower hole in support disk 682 is also sized to support its electrode rod 670 in a first hole section and the outer diameter of the outer tube 679 in a close fitting counterbore in an outer second hole section. The lower electrode rod 670, which is isolated from the fluid, serves as a reference, while the upper electrode rod 670 serves as the measurement sensor.

A metallic or plastic cover 684 consists of, from its left end as seen in FIG. 10, a tubular neck 685 which serves as a cover for the wires 675, a transverse bulkhead and an enlarged right circular cylindrical tubular shroud with interior bore 686. The righthand interior end of cover 684 is provided with female threads threadedly co-mated with the male threads 645 of housing 640. Cover 684 serves to isolate and protect the electrical connections of the sensor device 630.

Figure 11:
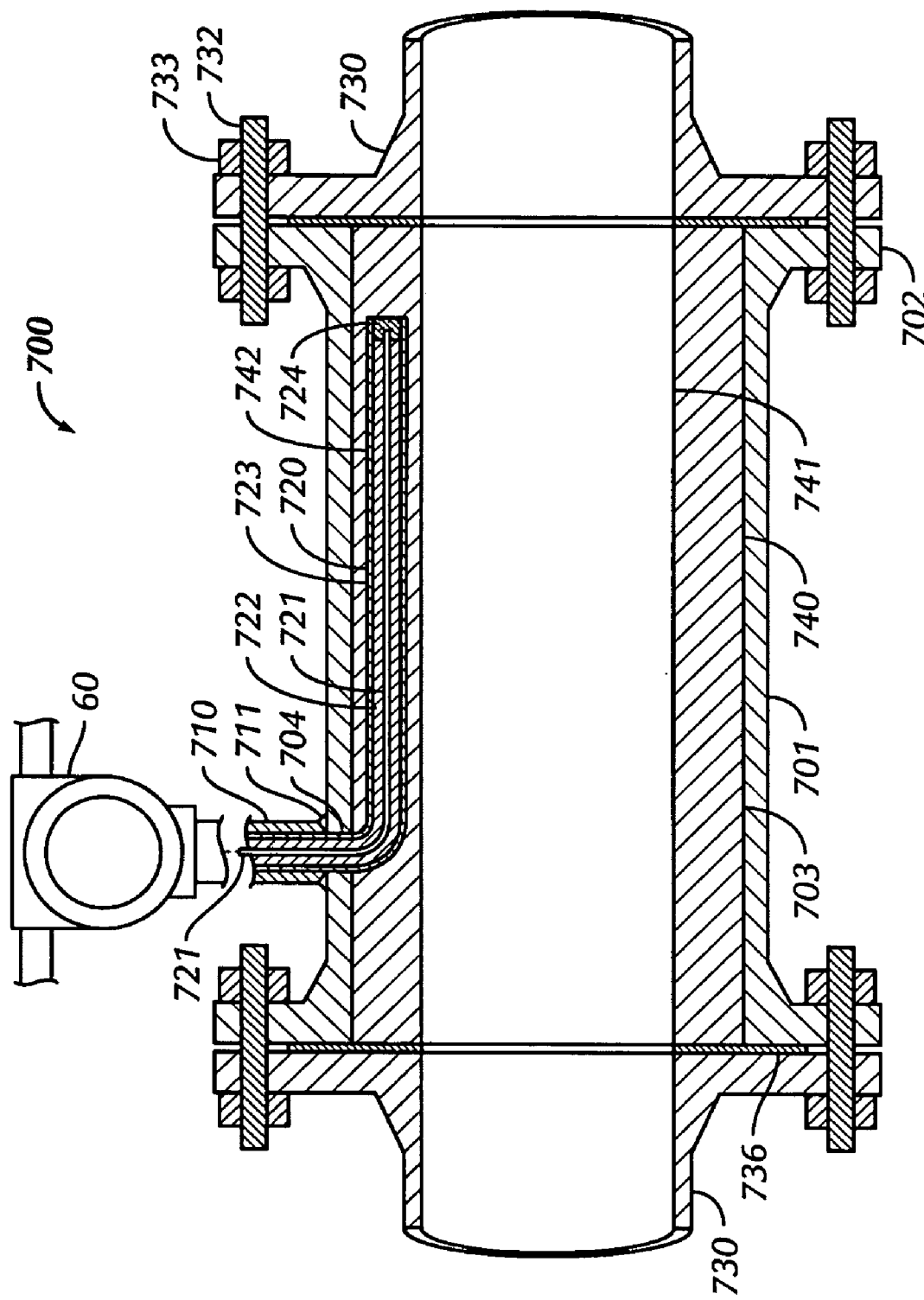
FIG. 11 is a partial longitudinal cross-sectional view of a fourth embodiment of the sensor device of the present invention, wherein the assembly is provided with a flanged full bore tubular flow through construction and the electrode is positioned parallel to the flow path.

FIG. 11 discloses a fourth embodiment 700 of the sensor device of the present invention, wherein a single sensor is embedded in the interior wall of the linear tubular flow through pressure containing housing. This particular embodiment 700, because of its unbranched constant-diameter straight flow path is particularly suitable for applications involving flowline plugging, line pigging, and other problematic situations.

A sensor body 701 is a right circular cylindrical tube having a transverse end flange 702 with a bolt hole circle located at each of its ends. The configuration of flanges 702 is consistent with either American Petroleum Institute (API) or American National Standards Institute (ANSI) standards or other applicable standards, so that they can be attached readily into a flanged flowline 730. A bore 703 of the tubular body 701 is concentric with the flanges 702 and is smooth and larger than the bores of adjacent co-matingly flanged end flowlines 730. A flat gasket 736 is used for sealing between each of the flanges 702 and its connecting flanged flowline 730 end. The flanges 702 are clamped sealingly to each other with threaded studs 732 engaged through the bolt hole circles of the flanges and threaded hex nuts 733. A radial circular hole 704 extends through the wall of body 701 close to one flange 702 and a pipe nipple 710 is welded concentrically with hole 704 onto the outside of body 701 with a circumferential weld 711. The outer end (not shown) of pipe nipple 710 is either threaded or flanged to permit the mounting and sealing of the electronics instrumentation 4 of the sensor device 700.

Sensor 720 is of tubular construction, with a concentric center electrically conductive cylindrical electrode 721, an electrically conductive cylindrical outer tubular sheath 723 and an insulative dielectric annular insulator 722 filling the annulus therebetween. The structure of the connection of sensor 720 to the instrumentation housing or enclosure 60 is the same as is shown in FIGS. 1 and 3. An electrically nonconductive sensor end cap 724 of right circular cylindrical configuration is press fitted into the distal end of the sensor 720. A blind hole to accommodate the distal end of the center electrode 721 is provided on the inner end of the end cap 724.

Sensor 720 is radially extended into the interior of the sensor body 701 through pipe nipple 710 and then its inner end is bent in an arc to lie parallel to the axis of body 701 and offset therefrom. The offset of the inner end of the sensor 720 is such that it lies at a median diameter in the annulus between the bore of the flowlines 730 and the bore 703 of the body 701. An electrically nonconductive body liner 740 is a concentric right circular cylindrical sleeve having an outer diameter snugly fitting bore 703 of body 701 and an inner diameter 741 equal to the inner diameter of the flowlines 730. A sensor pocket 742 has a radial outward opening and is conformed to be a close fit to the exterior of sensor 720. The body liner 740 is preferably constructed by casting it into the body 701 and around the preinstalled sensor 720.

Figure 12:
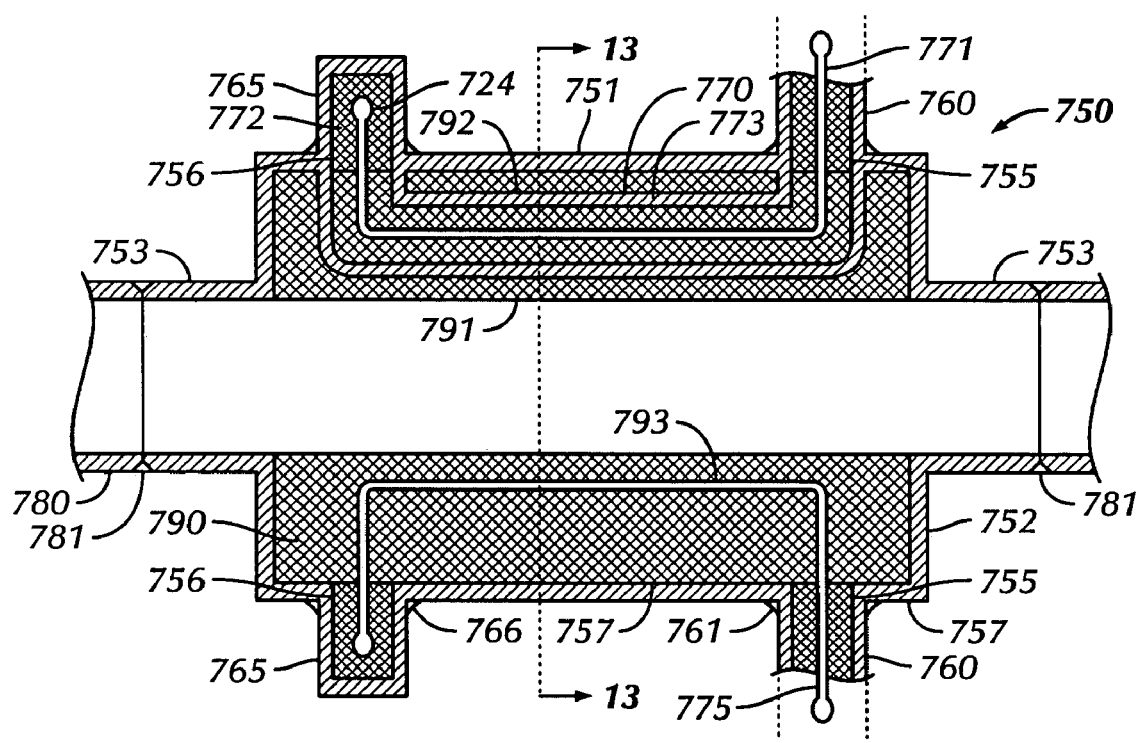
FIG. 12 is a longitudinal cross-sectional view taken through the electrodes of a fifth embodiment of the sensor device.
Figure 13:
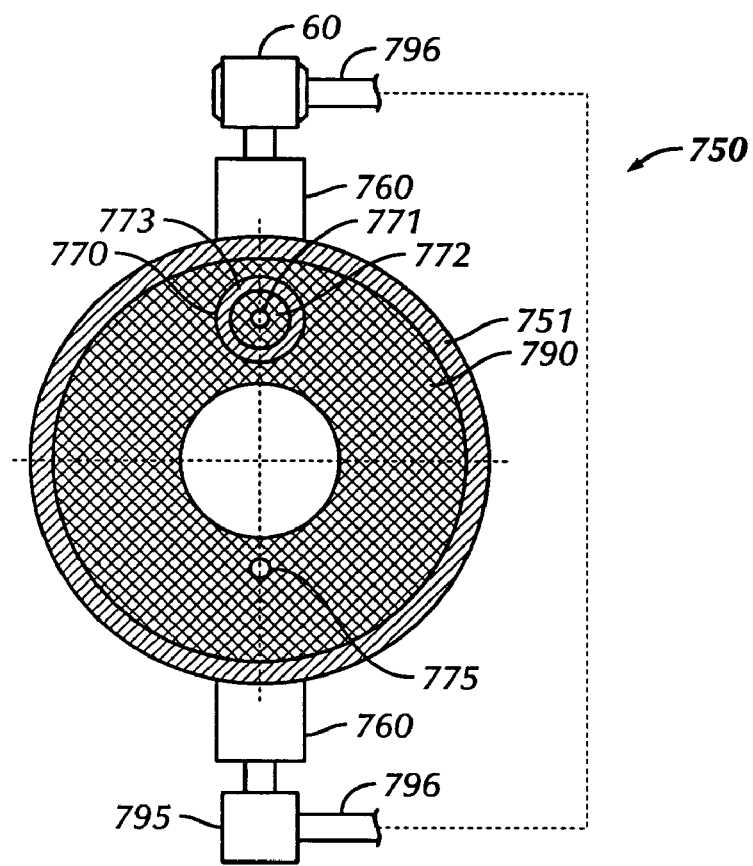
FIG. 13 is a transverse cross-sectional view of the fifth embodiment taken along the line 13—13 of FIG. 12, wherein two electrodes are deployed in diametrically opposed positions parallel to the flow path.

FIGS. 12 and 13 disclose a fifth embodiment 750 of the sensor device, wherein a single measurement sensor 770 and a single reference sensor 775 are embedded at diametrically opposed positions in the interior liner wall of the linear tubular flow through pressure containing housing. Although a sensor device body 751 is somewhat different than that of the fourth embodiment 700, the sensor configuration of this fifth embodiment primarily differs in the inclusion of the reference sensor 775. This particular embodiment 750, because of its unbranched constant-diameter straight flow path also is particularly suitable for applications involving flowline plugging, slurries or sandy flow, line pigging, and other problematic situations.

Tubular sensor device 750 is configured to be welded into place in a flowline 780 by means of circumferential welds 781. Housing body 751 consists of a central enlarged right circular tubular section having a transverse end diaphragm 752 and an attached concentric reduced diameter right circular tubular attachment neck 753 attached to each end. The outer ends of the attachment necks 753 are each provided with a weld prep for circumferential weld 781.

Two diametrically opposed radial circular holes 755 extend through the wall of body 751 close to the first transverse end diaphragm 752 of housing 751 and pipe nipples 760 are welded concentrically with holes 755 onto the outside of body 751 with circumferential welds 761. The outer end (not shown in FIG. 12) of each pipe nipple 760 is either threaded or flanged in order to permit the support of and sealing to a sensor 770 or 775 and the mounting of the electronics instrumentation 4 in the instrumentation housing 60 on a first nipple or the mounting of an explosion-proof junction box 795 on a second nipple. Junction box 795 holds the termination of the reference sensor 775 to a cable connection (not shown) going to the electronics instrumentation 4 via a conduit 796. Two other diametrically opposed radial circular holes 756 lie in the same plane defined by the housing longitudinal axis and the holes 755. Holes 756 are close to a second transverse end diaphragm 752 of the housing 751. Capped pipe nipples 765 are welded concentrically with holes 756 onto the outside of body 751 with circumferential welds 766. Although shown as one-piece, the capped nipples could have screw-on caps to simplify fabrication.

The measurement sensor 770 is of tubular construction, with a concentric center electrically conductive cylindrical electrode 771, an electrically conductive cylindrical outer tubular sheath 773 and an insulative dielectric annular insulator 772 filling the annulus therebetween. The structure of the connection of sensor 770 to the electronics instrumentation 4 is the same as shown in FIGS. 1 and 3. The electrically nonconductive sensor end cap 724 of right circular cylindrical configuration is press fitted into the distal end of the electrode 771. A blind hole to accommodate the distal end of the center electrode 771 is provided on the inner end of the end cap 724. Sensor 770 is radially extended into the interior of the sensor device body 751 through the first pipe nipple 760 and then its central portion is bent in an arc to lie parallel to the axis of body 751 and offset therefrom. The offset of the inner end of the sensor 770 is such that it lies at a median diameter in the annulus between the bore of the flowlines 780 and the bore of the tubular attachment necks 753 of the body 751. The distal end of sensor 770 is also bent in an arc so that it projects radially outwardly and enters into the interior of the capped nipple 765.

Reference sensor 775 consists of a single unshrouded cylindrical electrode inserted into the interior of housing 751 through the second pipe nipple 760. Reference sensor 775 is radially extended into the interior of the sensor body 751 through second pipe nipple 760 and then its central portion is bent in an arc to lie parallel to the axis of body 751 and offset therefrom. The offset of the inner end of the sensor 775 is such that it lies at a median diameter in the annulus between the bore of the flowlines 780 and the bore of the tubular attachment necks 753 of the body 751. The distal end of sensor 775 is also bent in an arc so that it projects radially outwardly and enters into the interior of the capped nipple 765.

An electrically nonconductive body liner 790 is a concentric right circular cylindrical sleeve having an outer diameter snugly fitting bore 757 of body 751 and an inner diameter 791 equal to that of the flowlines 780. A sensor pocket 792 has radial outward openings and is conformed to be a close fit to the exterior of sensor 770. A reference sensor pocket 793 is similarly configured, but closely fits to the reference sensor 775, and is located in a diametrically opposed position to that of sensor pocket 792. The body liner 790 is preferably constructed by casting it into the body 751 and around the preinstalled sensor 770 and reference sensor 775.

Figure 14:
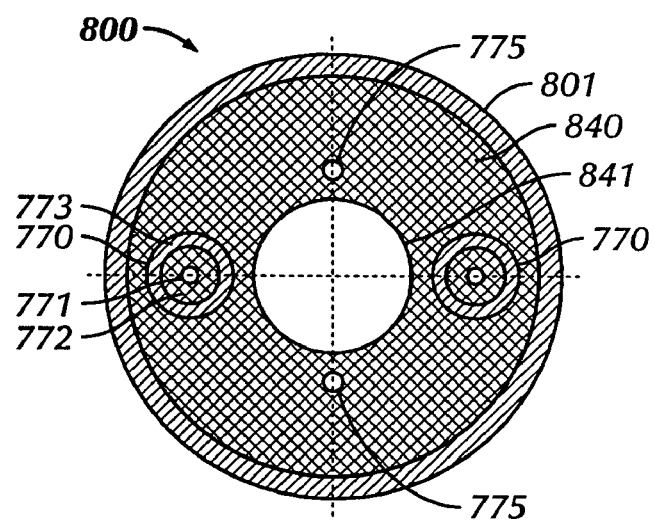
FIG. 14 is a transverse cross-sectional view of a sixth embodiment of the sensor device wherein four electrodes are arrayed parallel to the flow path.

FIG. 14 discloses a sixth embodiment 800 of the sensor device, wherein dual measurement sensors 770 and dual reference sensors 775 are respectively embedded at diametrically opposed positions in the interior liner wall of the linear tubular flow through pressure-containing housing 801. The angular spacing of the measurement sensor pair 770 from the reference sensor pair 775 is 90 degrees. Although the sensor device 800 is somewhat different from the fifth embodiment 750, the sensor configuration of this sixth embodiment differs only in the inclusion of multiple measurement and reference sensors. Likewise, housing 801 and a liner 840 differ only in their accommodation of the additional sensors. The second measurement sensor 770 is provided with a conduit and wiring connection for communication to the electronics instrumentation. This particular embodiment 800, because of its unbranched constant-diameter straight flow path, is also suitable for applications involving flowline plugging, slurries or sandy flow, line pigging and other problematic situations.

Figure 15:
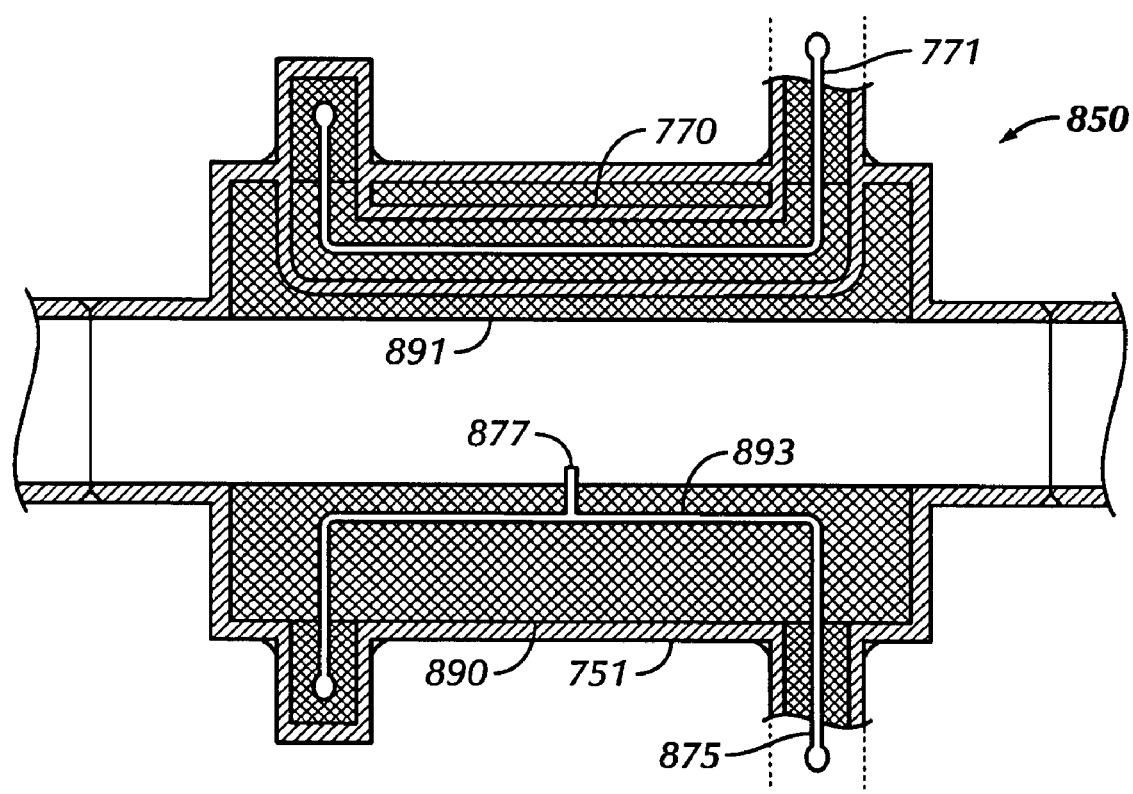
FIG. 15 is a longitudinal cross-sectional view of a seventh embodiment of the sensor device of the present invention.

FIG. 15 discloses a seventh embodiment 850 of the sensor device, wherein the measurement sensor 770 and a reference sensor 875 are respectively embedded at diametrically opposed positions in the interior liner wall of the linear tubular flow through a pressure-containing housing 751. Although the sensor device 850 is somewhat different that that of the fifth embodiment 750, the sensor configuration of this seventh embodiment 850 differs only in the alteration of a reference sensor 875 and its consequential change in its embedment in a body liner 890. For sensor device 850, the reference sensor 875 has an inwardly projecting electrode part 877 extending into a throughbore 891 of the sensor device 850 so that the electrode part 877 is in intimate contact with the fluid flowing through the sensor device 850. The electrode part 877 is centrally positioned in the section of the reference sensor 875 which is parallel to the longitudinal axis of the sensor device 850. The body liner 890 has a reference sensor pocket 893 modified from the otherwise similar pocket 793 in the body liner 790 of the fifth embodiment 750 of the sensor device. The modification to pocket 893 consists of a radial inward hole projecting into the bore 891 of the body liner 890. The radial inward hole provides a close fit to the inward projection 877. This particular embodiment 850, because of its unbranched constant-diameter straight flow path, is also particularly suitable for applications involving flowline plugging, slurries or sandy flow, line pigging and other problematic situations.

Figure 16:
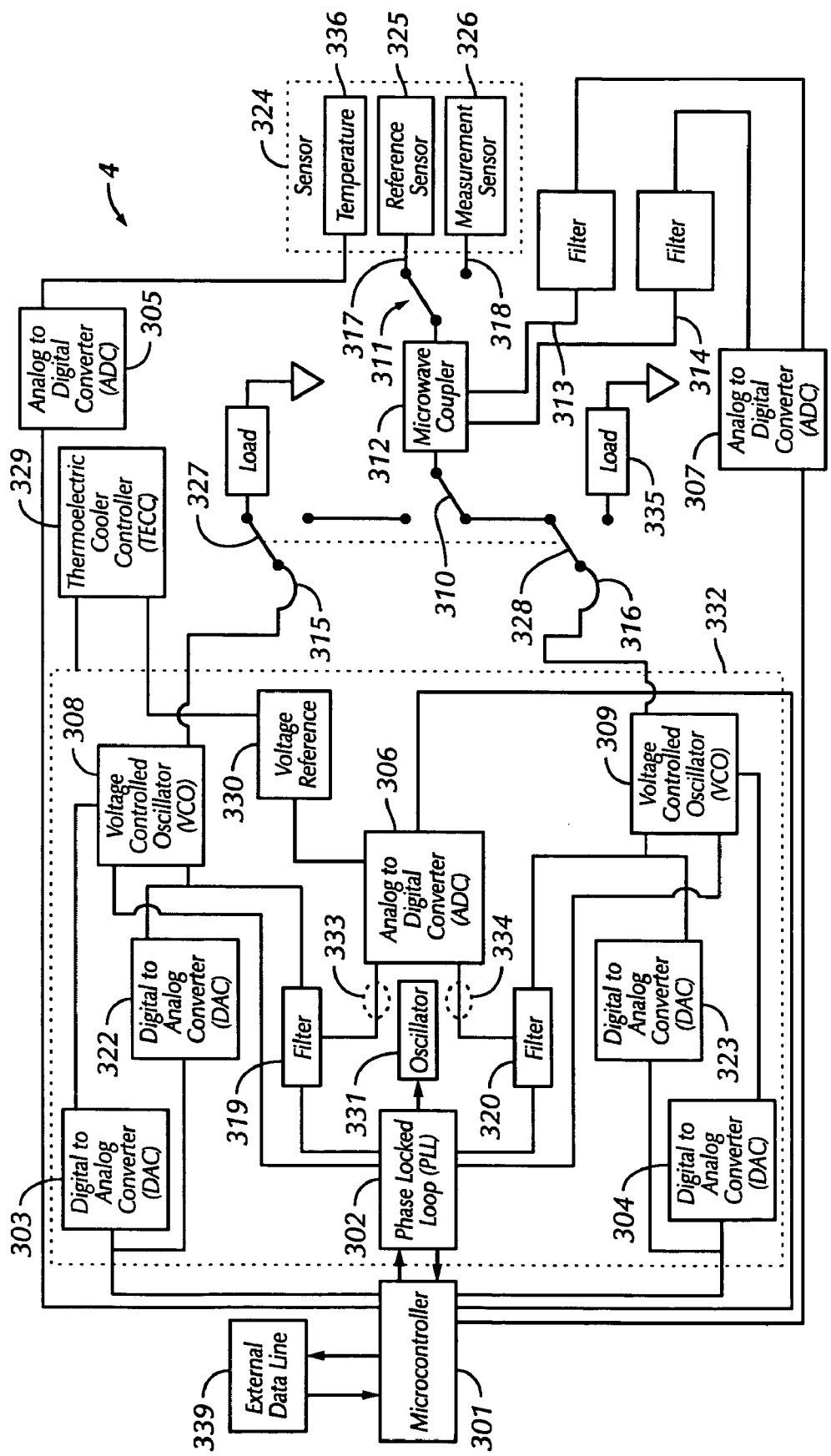
FIG. 16 is an electrical circuit schematic for the present invention.
Figure 17:
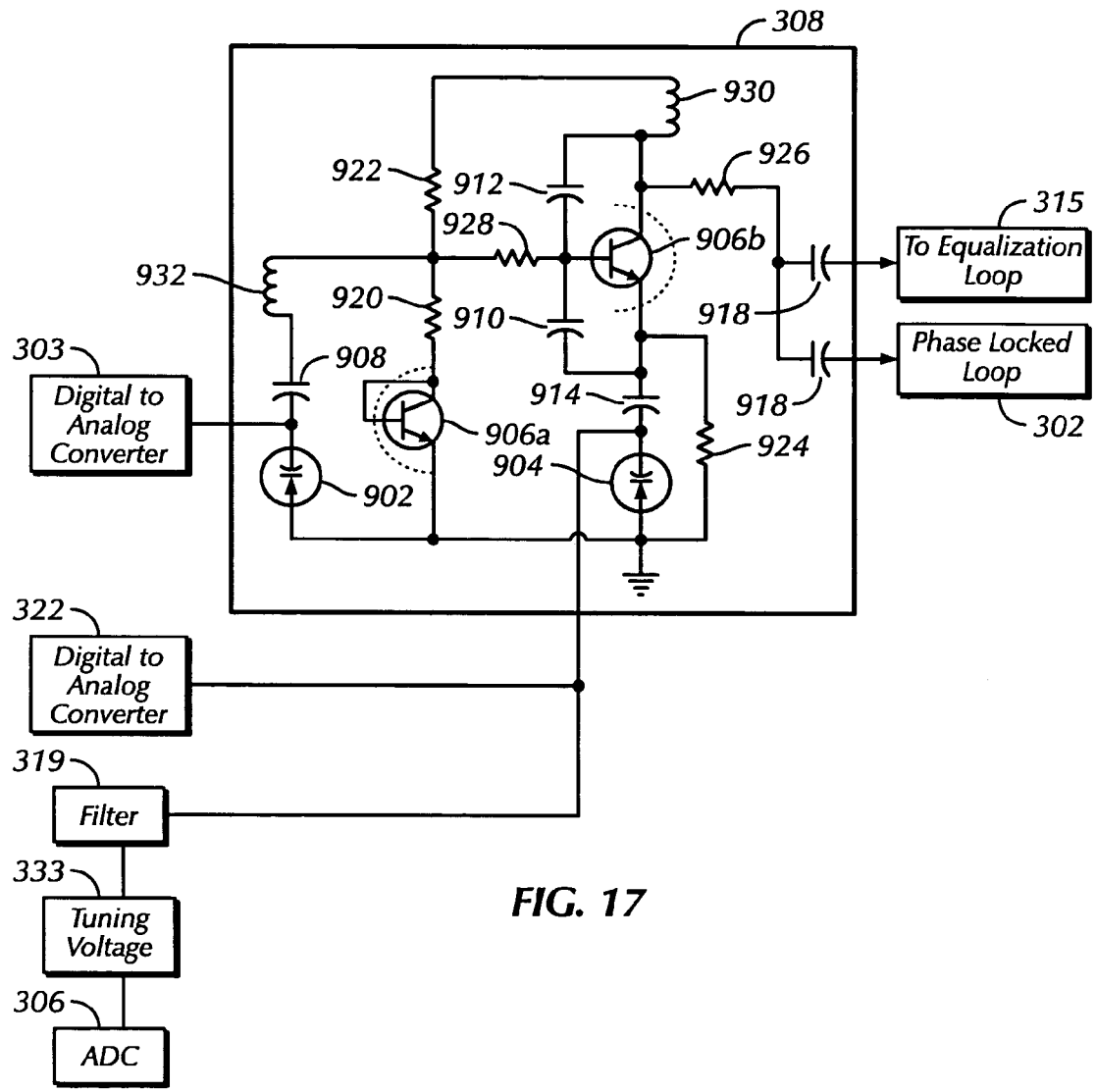
FIG. 17 is a schematic representation of the voltage controlled oscillator for the present invention.

FIG. 16 shows an electrical schematic of the electronics instrument package 4 described below. Similarly, FIG. 17 illustrates a schematic representation of the voltage controlled oscillator 308 that is described in detail below.

OPERATION OF THE INVENTION

For illustrative purposes, the sensor device 1 of the first embodiment of the present invention (FIGS. 1, 2 and 4) is installed in an oil pipeline 201 and the fluid mixture is primarily oil and water. The flange 70 of probe mounting support 3 is bolted to the upper flange of the ball valve 203 with a conventional gasket seal to effect a sealing connection between the probe mounting support 3 and the ball valve 203 (bolts not shown). For the probe mounting support 3, the seal activating hex nuts 87 can be loosened to relieve the friction of the packing rings 81 on shaft 6 of probe 2 so that the axial position of the probe 2 can be inserted at the desired radial position within the pipeline 201. At that point, the seal-activating hex nuts 87 are tightened sufficiently so that packing rings 81 will both seal between the shaft 6 and the seal housing 74 and also produce sufficient friction between the packing rings 81 and shaft 6 to restrain the shaft 6 against further axial movement.

Once the sensor head 15 has been installed in the pipeline 201 and its position adjusted appropriately, the lower tip of sensor head 15 will protrude below the lower face of flange 70 and past the inner wall of the fluid conduit so that the shield 17 of the sensor head 15 of the probe 2 is fully exposed to the flow of the fluid to be measured. The slots 23 in the shield 17 permit the circulating fluid to freely enter and exit the annular space between the probe rod 34 and shield 17. Some turbulence is created in the fluid entering this annular space so that more uniform local mixing and hence representative fluid dielectric properties are obtained. The combination of the shield 17 and the probe rod 34 are insulated from each other within the probe 2 and so function as a cable having a dielectric therebetween.

For the second embodiment 100 of the present invention, the operation is very similar to that of the first embodiment 1. The only substantial difference between the two embodiments is that the a seal housing 174 of a probe mounting support 103 is connected to a female threaded boss or a hot tap fitting (not shown) attached to the fluid conduit by means of a male thread 170 of the probe mounting support 103.

The present invention relates to an improved method and apparatus utilizing signals, such as microwave or radio frequency, to facilitate the analysis of a fluid mixture, such as oil and water, where the fluid can also contain salt and sulfur compounds. The present invention, therefore, also determines the salt and sulfur content of the fluid mixture as well as the density and temperature of the mixture. The analysis is performed by evaluating the complex permittivity of individual fluid components.

The structure of the dual-sensor probe 324 is shown in FIG. 6 and the inter-workings of the accompanying components of the electronics instrument package 4 are shown in FIG. 16. In the present invention, software-controlled phase locked loop(s) (PLL) 302 are used to control oscillator circuits which are coupled via transmission lines 317 and 318 to the dual-sensor probe 324 which is immersed into the fluid mixture being analyzed.

Probe 324 is a differential measurement system, consisting of reference sensor 325 and measurement sensor 326 which are contained within the same sensor body 409. Each sensor 325 and 326 has a transmission line (e.g., the reference transmission line 317 and the measurement transmission line 318) through which signals, such as radio frequency or microwave, are communicated to electrodes 412 and 411 of sensors 325 and 326, respectively.

The sensor body 409, containing sensors 325 and 326, has the form of a slotted cage through which the fluid mixture flows. Sensor body 409 serves as an outer conductor such that the fluid acts as the dielectric between the inner conductor (measurement electrode) 411 and the outer conductor (sensor body) 409. The cage diameter is sized such that the dielectric constant of oil for the conductor formed by the inner conductor 411, the outer conductor or sensor body 409 and the fluid (assuming that it is 100% oil) produces minimal impedance mismatch with the connecting measurement sensor transmission line 318. Nominally, the impedance of the measurement sensor 326 formed with the slotted probe 324 is about 50 ohms when immersed in oil. Because the slots 423 are small relative to the wavelengths used, a microwave field for the measurement sensor 326, for instance, is primarily contained within the walls of the cage. Consequently, nearby metal objects, such as the wall of pipe (not shown), effectively do not influence the measurements.

Changes in the complex permittivity of the fluid mixture act as an impedance in parallel with the resonant elements of the oscillators, thus changing their resonant frequencies. The change in measurement probe impedance tends to cause the frequency to deviate or to "pull" the frequency of the oscillator(s) away from the frequency set by the microcontroller 301. Such devices are commonly referred to as load pull oscillators. This design differs from other designs (Scott et al., U.S. Pat. Nos. 5,025,222, 4,996,490, and 4,862,060) in that it does not allow the voltage controlled oscillators 308 or 309 to change frequency and thus a change in frequency cannot be measured. This is important because of dispersion, where the property being measured changes as the measuring frequency changes. Dispersion is defined as the change of permittivity for the measurement sensor 326 as a function of frequency.

This oscillator is made adjustable by using a varactor in the oscillator's resonant tank. Oscillators of this type are called voltage controlled oscillators or VCOs 308 and 309.

As the VCO is pulled by changes in the dielectric constant of the medium, the PLL 302 automatically changes the voltage applied to the varactor to bring the VCO back to the frequency set by the microcontroller 301. The PLL 302 compares the frequency set with a very accurate crystal oscillator 331, which can be made still more accurate by maintaining it at a constant temperature using something like a thermoelectric cooler (TEC) 332 which is controlled by a thermoelectric cooler controller (TECC) 329. The voltage required to maintain the PLL 302 at its set frequency is then measured. This required voltage is called the tuning voltage 333 and 334, which is a direct measurement of the amount of "pull" asserted on the VCO by the permittivity (impedance) of the fluid medium. Thus, tuning voltages, such as 333 and 334 in FIG. 16, are directly related to the complex permittivity of the multi-component fluid mixture.

Maintaining a constant frequency of the VCOs 308 and 309 insures that the measurements are not affected by the dispersion of the complex permittivity of the fluid mixture. Because these frequencies are accurately selected under software control by the microcontroller 301, behavior of expected fluid mixture components at that sensor-exciting frequency can be known a priori from study in a controlled laboratory setting. Likewise, any non-linear behavior of the varactor also can be measured and compensated for by means of the software for the microcontroller 301.

Because one of the objectives of the present invention is to measure concentrations of liquids flowing in some form of conduit, such as pipeline 201, the components and the concentrations of the components of the fluid are expected to vary over time. It is important to make very rapid and frequent measurements in order to accurately track the variations in component concentrations. The use of the PLL 302 allows rapid frequency changes and accurate frequency locks (stabilizations) within a given frequency range for both the measurement 326 and reference 325 sensors. However, it is often necessary to use additional, separate VCOs to cover different frequency ranges. This availability of different oscillators allows rapid switching to widely differing frequency ranges so that nearly concurrent permittivity measurements can be made.

The complex permittivity of various components of the fluid mixtures varies as a function of frequency. Some fluid component permittivities vary significantly with frequency while others remain relatively constant. The sensor device of the present invention exploits this difference in frequency response by making multiple, effectively concurrent, measurements at various frequencies. Using the measured permittivities at the selected measurement frequencies, fluid component concentrations can be determined by solving a set of mathematical equations or by looking them up in a previously calculated table of values.

Because permittivity is a complex term in the mathematical sense, it has both real and imaginary parts. Accordingly, three parameters must be measured at each frequency to provide sufficient information to define these terms. These three measurements are determined by the complex permittivity, which is directly related to the impedance of the fluid medium as measured by the measurement sensor 326.

The first measured parameter is the tuning voltage such as 333 and 334, mentioned previously as the voltage output from the PLL 302 when the frequency is locked, which represents primarily the real part of permittivity. The second measured parameter, representing primarily the complex part of permittivity, is called reflected voltage, which is a measure of the reflected power from the unbuffered probe 324 along a reflected signal line 314. The reflected power is filtered and sent through DAC 307 to convert the power signal into binary numbers for manipulation by the microcontroller 301. The third measured parameter is the forward voltage, which is a measure of the incident power to the unbuffered probe 324 along a forward signal line 313. The incident power is also filtered and sent through DAC 307 to convert the power signal into binary numbers for manipulation by the microcontroller 301.

Forward and reflected power measurements are accomplished by placing an RF, microwave or similar coupler 312 in the transmission line 317 and/or 318. The use of the coupler 312 allows diversion of part of the signal in the transmission line 317 or 318 for measuring reflected voltage without interfering with the connected primary signal path. Variations in complex permittivity as a function of probe-exciting frequency, known as dispersion, can occur in either the real or imaginary parts of the complex permittivity, thereby making it possible to distinguish between some very similar materials. For example, both sulfur compounds and oil have very low imaginary parts of permittivity, but significantly different real permittivity parts. By comparison, water has both higher real and imaginary parts of its complex permittivity.

Because the change in the complex impedance of the oil and water mixture is not monotonic with respect to changes in the ratio of oil to water, use of a single frequency measurement will introduce ambiguity in calculating the ratio of oil to water. As mixtures of oil and water have different characteristics at different frequencies, by using multi-frequency measurements, this ambiguity can be removed.

Sampling intervals must be short enough compared to the flow rate of the oil and water mixture so that measurement errors from fluid non-uniformity are not introduced. In the present invention, the microcontroller 301 controls the PLL 302 with a desired frequency range that can be too wide for a suitable single VCO. Therefore, multiple oscillators are used and switched on and off the transmission lines 317 and 318 as necessary. By switching between VCOs 308 and 309, for example, the frequency of one oscillator may be changed while the other is making a measurement so that measurements can be made almost continuously. More oscillators can be added (not shown) in a similar manner.

Effects of temperature and pressure changes in the fluid and the elongation of the connecting transmission lines 317 and/or 318 are compensated by switching between the measurement sensor 326 and the reference sensor 325 of the probe 324 with their attached cables 318 and 317, respectively. Because the reference sensor 325 should always produce the same frequency pull in the oscillator if fluid temperature and pressure and line length are the same, the measurement sensor 326 is switched to the oscillator and the tuning, forward and reflected voltages are measured. These voltages are compared by the microcontroller 301 to the encoded factory-calibrated values and a correction factor is calculated and applied to all subsequent measurements until a further update is made.

The dual-electrode probe 324 (FIGS. 6 and 16) consists of the reference sensor 325 and the measurement sensor 326 being assembled in the same housing 409. The reference sensor 325 and the measurement sensor 326 have identical transmission lines 317 and 318, respectively, through which radio frequency, microwave or other types of signals are communicated to the electrodes 411 and 412 of the sensors 325 and 326, respectively. These electrodes 411 and 412 are identically dimensioned for both sensors 325 and 326, but the reference sensor 325 has a continuous electrically-conducting jacket 413 surrounding the electrode 412. The gap between the electrode 412 and its outer jacket 413 is filled with plastic material 414, such as Teflon or TPX, which has complex permittivity close to that of dry oil. In contrast, slots 423 are cut into the electrically conductive jacket 409 of the measurement sensor 326, forming a cage surrounding the axial electrode 411, so that fluids can flow between the cage and measurement electrode 411.

The radio frequency, microwave or other signal from the oscillator is sent to the reference sensor 325 or to the measurement sensor 326 using an electronic switch 327 or 328 controlled by the microcontroller 301. In both cases, parameters of forward signals and reflected signals are measured by the VCO 308 or 309, and the complex permittivity of the fluid contained within the measurement sensor 326 is calculated. The reference sensor 325 is used to compensate for: a) aging and/or drift of measuring electronics, b) fluid pressure and temperature influence on feeders and seals, and c) elongation of connecting cables, transmission lines, etc. Additional means of compensation and calibration of the electronics are described in a separate section.

In another embodiment, the measurement electrode 411 of the measurement sensor 326 can be isolated from the mixture of fluids by covering it with a thin layer of dielectric to adjust sensitivity of the sensor 326 to the desirable range.

In another embodiment, the radio frequency, microwave or other signals from the oscillator can be multiple frequencies with a preset frequency ratio pattern 1:2:3:4 . . . RF, microwave or other excitation signals sent to and reflected from the reference sensor 325 or the measurement sensor 326 can be measured at these different frequencies to increase the accuracy of concentration calculations. In essence, the energy travels down the transmission line 317 or 318, is reflected and travels back to the source of the signal. A radio frequency, microwave or other signal coupler 312 separates the signal direction for measurement.

In another sensor device, the probe 500, as shown in FIG. 8, has two measurement sensors 326 that measure different properties of the fluid mixture—such as, density, viscosity, conductivity, sulfur, etc. In yet another embodiment (FIG. 9), the probe 600 has multiple measurement sensors 326 with different types of measurement electrode coatings, differing by thickness, shape, complex permittivity, etc. In yet another embodiment (not shown), the probe has two or more measurement sensors differing by using different types of electrical load at its end: a) capacitance, b) inductance, c) resistance, d) short circuit, etc. In yet another embodiment (not shown), the probe is connected to the measurement electronics using length of lines equal to multiple half wavelengths of the lowest measuring frequency. The lengths of reference and measurement transmission lines, called equalization lines, are independently adjustable so that the shaft length of the insertable/retractable measurement apparatus can be adjusted to a required shaft length. Shaft lengths depend upon the necessary position of the probe sensors inserted in the fluid medium. Use of equalization lines allows virtually any shaft length and any set of frequencies to be used with the probe. However, many times the transmission or equalization lines are adjusted to be an equal length to each other.

Detailed Explanation of the Electronic Calibration

As an on-line oil/water detector system, large and sometimes rapid temperature changes can be expected. Since this equipment will be used for custody transfer of oil products involving large sums of money, extreme accuracy and repeatability are of paramount importance. Accuracy and repeatability have been a problem for many systems based upon microwave techniques, particularly those using load-pull oscillators, which often required weekly calibration. Arguably, calibrating more often might be desired in some cases, except for the expense and logistics involved are prohibitive. Much effort has gone into the design of this equipment to mitigate the effects of aging and thermal drift and to simplify and automate the error detection and calibration processes. The following paragraphs emphasize and explain these methods.

For clarity, the description of the electronics operation of the electronics instrumentation 4 of FIG. 1 is briefly reiterated in the following paragraphs, then specific sections of the electronics having to do with the electronics calibration or maintaining the accuracy and stability of the sensor device are discussed in detail. An overall instrument diagram illustrating the interconnections of the sensor device and the electronics instrumentation is shown in FIG. 16.

Microcontroller 301 (which may be a traditional microcontroller or a combination of intelligent signal processors, controllers and logic) programs the phase locked loop (PLL) 302 to specific operating frequencies. Output currents from the PLL 302 pass through filters 319 and 320 to form the tuning voltage 333 and the tuning voltage 334 that control the voltage controlled oscillators (VCOs) 308 and 309 respectively.

VCO 308 and VCO 309 output frequencies through the equalization loops 315 and 316 to RF Switches 327, 328 and 310. RF Switches 327, 328, and 310, under microcontroller 301 control, select VCO 308 or VCO 309 to transmit through the microwave coupler 312 to RF Switch 311. RF Switch 311, also under Microcontroller 301 control, routes VCO 308 or VCO 309 output signals through either the reference transmission line 317 or the measurement transmission line 318 to either the reference sensor 325 or the measurement sensor 326 of probe 324.

The measurement probe 324 is in intimate contact with the fluid to be measured. The fluid to be measured affects the frequency output from VCO 308 or VCO 309 by changing the impedance loading the oscillator. As VCO 308 or VCO 309 are pulled off frequency, the PLL 302 detects the error by comparing the VCO output frequency to a very stable crystal oscillator. The frequency error is corrected by the PLL 302 outputting currents to filters 319 and 320 that convert the currents to a smoothly changing voltage that is applied to restoring devices inside the VCOs to force the frequency back to that set by microcontroller 301.

The filters are tuned to provide optimal PLL characteristics for this application, such as the optimal lock time, range, settling time, etc., but also include additional elements to provide filtering and buffering for the analog to digital converter (ADC) 306. The ADC 306 converts the tuning voltage 333 and the tuning voltage 334 into binary numbers for manipulation by the microcontroller 301. When either the VCO 308 or the VCO 309 are connected to the reference sensor 325, any change in tuning voltages 333 or 334 must be due to either the temperature or pressure of the fluid. Although the reference sensor 325 is not in intimate contact with the fluid being measured, it does experience the same pressures and temperatures that the measurement sensor 326 experiences. The reference temperature detector (RTD) 336 is also part of the sensor probe 324 and experiences the same fluid temperature as the two sensors, but does not respond to pressure changes. Therefore, temperature induced changes in VCO 308 and VCO 309 outputs and pressure-induced changes can be individually ascertained by software in microcontroller 301. The ADC 305 converts the temperature measurement from an analog signal to a digital signal. This improves the accuracy and repeatability of the measurement.

An external data line 339 is used to connect devices to the microcontroller 301 when a firmware update is required or when connection to an external system is desired.

The probe is connected to the measuring electronics by using coaxial lines having a length equal to multiple half wavelengths of the lowest measuring frequency. The lengths of the reference and measuring coaxial lines, labeled equalization loops 315 and 316 in FIG. 16, are independently adjustable so that the shaft length of the insertable/retractable/measuring apparatus can be adjusted to a required shaft length. Shaft lengths depend upon the probe position necessary to measure the fluid medium. Use of equalization lines allows virtually any shaft length and any set of frequencies to be used with the probe.

If a ratio of wavelengths is desired, then equalization loop 315 and equalization loop 316 allow the length of the reference transmission line 317 or the measurement transmission line 318 to be adjusted. This may be appropriate when a specific voltage standing wave is needed or in order to optimize a sensor configuration.

When VCO 308 and VCO 309 exhibit thermal drift, it is virtually impossible to distinguish that drift from signal changes in the fluid. These VCOs are intentionally made very sensitive to loading so that small changes in fluid mixture are detectable. Unfortunately, this reduces or removes the feedback elements used to improve linearity and temperature stability. In addition to compensating for fluid temperature and pressure changes, there are several techniques used in the present invention to compensate for drift in the electronics that restore the absolute accuracy of the system as distinguished from the relative accuracy.

Referring to FIG. 16, the digital to analog converters (DAC) labeled as DAC 303, DAC 304, DAC 322 and DAC 323 are controlled by the microcontroller 301 to reduce the temperature and aging effects of VCO 308 and VCO 309. DAC 322 and DAC 323 are of a type that can be set with high impedance output when not in use so that they have no influence on the VCO 308 and VCO 309 shown schematically in FIG. 16. Instead, the PLL 302 has complete control. When in a test mode, low impedance outputs of DAC 322 and DAC 323 are switched on and modified by microcontroller 301, overriding any PLL influence. This process is commonly referred to as "breaking the loop", specifically, the control loop of the phase locked loop. In this way, DAC 322 and DAC 323 can be changed and the response of the VCOs measured.

This measurement is accomplished by placing buffer amplifiers in filter 319 and filter 320 so that the ADC 306 can measure the correction that would have been applied by PLL 302 to VCO 308 or VCO 309 even while DAC 322 and DAC 323 are controlling them. Transfer function curves (plotting the $V_{in}$ versus the $V_{out}$) are generated for VCO 308 and VCO 309 that can be compared to the transfer function curves generated for VCO 308 and VCO 309 when the on-line oil/water sensor device was calibrated at the factory. The microcontroller 301 periodically initiates tests for temperature drift or component aging of VCO 308 and 309. Any detected drift is then corrected by the microcontroller 301.

Exactly how this correction is accomplished is illustrated in FIG. 17, a schematic illustration of VCO 308 from FIG. 16. The DAC 322 overrides filter 319 to take over control of the varactor 904 so that the transfer function of VCO 308 can be measured as described previously.

The microcontroller 301 sets DAC 322 to a known and very repeatable set of voltages that modifies the capacitance of the varactor 904 in FIG. 17 to generate a measured transfer function for VCO 308. The measured transfer function is compared to the expected or original transfer function. The deviation of the measured transfer function from the expected VCO transfer function is calculated by the microcontroller 301 and corrected subtracting the calculated deviation as each measurement is made. The resulting data will appear as if it was made using the original factory calibration of the VCO. This process represents one temperature control method for the sensor device.

Those familiar with the art will recognize the transistor structure of FIG. 17 as a VCO. Transistor 906b provides the oscillator gain element. The resonant tank of VCO 308 is made up of inductor 930 and capacitance formed from capacitor 908 and varactor 902. Capacitance formed by the series combination of capacitor 914 and varactor 904 will affect the frequency dependent gain of the transistor 906b and the frequency of oscillation. Resistors 922 and 920 provide a bias voltage and current to transistor 906b. Resistor 926 provides impedance matching between the oscillator and subsequent circuitry. Although there are numerous variants of the VCO design, the basic tenets described herein can likely be applied.

As the temperature of transistor 906b, changes the base to emitter voltage follows the following equation, which is good for over nine orders of magnitude:

$$Vbe = \frac{k}{q}\ln\left(\frac{Ic}{AT^3}\right) + Vgo$$

Where Vbe is the voltage measured between the base and emitter when the transistor is biased to get a collector current Ic to flow, k is Boltsman's constant $1.38 \times 10^{-23}$, q is the charge on an electron $1.6 \times 10^{-9}$ Coulombs, A is the area of the junction, T is the temperature in degrees Kelvin and Vgo is the bandgap voltage of silicon.

As the temperature of the transistor changes, Vbe changes so that the dc operating bias provided to transistor 906b by the resistor 922 and resistor 920 changes enough to cause changes in the frequency of the oscillator. It is impossible to distinguish this change from a change due to load pull from the sensor so it is important either to keep the transistor temperature constant or to compensate the circuit bias.

FIG. 17 shows a modification of the gain transistor's bias circuitry in order to provide temperature compensation. A matched pair of transistors, 906a and 906b, manufactured at the same time and encapsulated in the same package so that they see virtually the same temperature, have virtually the same drift with temperature. As the temperature of transistor 906b changes due to self-heating or to changes in ambient temperature, the Vbe changes will track one another and the voltage of the bias network on the base of 906b will remain constant. Bias resistor 928 can optionally be added as necessary to match the current through the two transistors. This is the second temperature control method.

FIG. 16 shows that three RF switches are used, switches 327, 310 and 328. When one side of RF switch 327 is switched to the microwave coupler 312, the other side is switched into a known load 335. In the preferred embodiment the known load is shown as 50 ohms, but may be a known impedance or length of coaxial cable. Thus, whichever VCO is switched to the known load is uncoupled from the loading effects of the sensor probe 324 and the reference transmission line 317 or the measurement transmission line 318. Assuming that the load is stable and constant with temperature, then whatever changes occur in VCO performance, as measured by changes in the tuning voltage 333 or tuning voltage 334, must be with respect to temperature and component aging within the VCO. Measurements are made using ADC 306 and any corrections that need to be made can be implemented using DAC 303 and DAC 304. Referring again to FIG. 17, DAC 303 would apply a voltage to varactor 902. Varactor 902 affects the frequency of VCO 308, but is independent of the PLL control path. Consequently, varactor 902 can be used to correct for frequency changes due to temperature or drift such that the tuning voltage 333 always remains the same. Because the correction is done at the sampling rate, it will correct minor drifts that occur between calibrations of the VCO transfer function as discussed previously. Digital filtering may be implemented in order to remove some of the measurement noise of this correction method. DAC 304 corrects VCO 309 in a similar manner. This is the third temperature control method.

Although the previously described temperature control methods may be adequate, the apparatus may be subject to very large ambient temperature ranges, from artic cold to desert heat. Maintaining temperature control of the more sensitive electronic components will enhance the overall system performance. This is accomplished by using a thermo electric cooler 332 (TEC) as shown in FIG. 16. TEC 332 is attached to the bottom of the printed circuit board containing block elements enclosed in the dashed line of FIG. 16.

Included in these elements is the voltage reference 330, which has a temperature output, used as a feedback path for the thermo electric cooler controller (TECC) 329. TEC 332 is capable of heating or cooling. So if the temperature exceeds a set point temperature, then the TECC 329, under microcontroller 301 control, outputs a current such that TEC 332 cools. Likewise, if the temperature drops below the set point temperature, TECC 329 changes the current so that TEC 332 increases its temperature. Because of this control, less stringent temperature requirements are imposed upon such things as the reference crystal oscillator 331 for the PLL 302 as shown in FIG. 16. To reduce power usage for the TEC 332, the printed circuit board is coated with a thermal insulator. Once a set point temperature has been achieved, very little power is needed to maintain that temperature.

Although the present invention and its advantages have been described in detail, it should be understood that various changes, substitutions and alterations can be made herein without departing from the spirit and scope of the invention as defined by the appended claims.

What is claimed is:

1. A sensor device for determining the concentration of fluid components within a fluid mixture comprising:
   a) a microcontroller;
   b) a sensor probe including:
      (i) a probe body having at least two fluid openings for allowing a fluid mixture to flow through the probe body,
      (ii) a measurement sensor within the probe body, the measurement sensor having a measurement electrode in communication with the fluid mixture and a measurement transmission line, and
      (iii) a reference sensor within the probe body, the reference sensor having a reference electrode in communication with a reference transmission line, wherein a portion of the reference electrode is covered by a reference isolator; and
   c) an electronics instrument package in communication with the microcontroller, the electronics instrument package having a signal generating/receiving unit in communication with the measurement transmission line and the reference transmission line, wherein the signal/receiving unit reciprocably activates the measurement electrode and the reference electrode to measure a parameter of the fluid mixture at a predetermined frequency, wherein the microcontroller calculates a permittivity of a component of the fluid mixture based on multiple measurements of the measured parameter by the reference sensor and the measurement sensor;
   whereby the microcontroller determines the concentration of the component in the fluid mixture using the calculated permittivity.

2. The sensor device of claim 1 further comprising a reference temperature detector within the probe body and in communication with the electronics instrument package.

3. The sensor device of claim 1, wherein a portion of the measurement electrode is exposed to the fluid mixture.

4. The sensor device of claim 1 having more than one measurement sensor within the probe body.

5. The sensor device of claim 4, wherein a portion of at least one of the measurement sensors is covered with a measurement isolating shroud.

6. The sensor device of claim 4, wherein a portion of one measurement electrode is exposed to the fluid mixture and a portion of one measurement electrode is covered with a measurement isolating shroud.

7. The sensor device of claim 4, wherein more than one measurement sensor is at least partially covered with a measurement isolating shroud and wherein the isolating shroud of each measurement sensor has a wall thickness that differs from the isolating shroud of any other measurement sensor in the sensor device.

8. The sensor device of claim 4, wherein the electronics instrument package includes a means for automatically selecting the measurement sensor to be activated, the selection based on the measured parameter of the fluid mixture.

9. The sensor device of claim 1 having more than one reference sensor within the probe body.

10. The sensor device of claim 1 having more than one reference sensor and more than one measurement sensor within the probe body.

11. The sensor device of claim 1, wherein a load on the measurement transmission line and the reference transmission line is independently adjustable.

12. The sensor device of claim 1, wherein a length of the measurement transmission line and the reference transmission line is independently adjustable.

13. The sensor device of claim 1, wherein a length of the measurement transmission line and the reference transmission line is substantially equal.

14. The sensor device of claim 1, wherein the predetermined frequency includes multiple frequencies.

15. The sensor device of claim 14, wherein a length of the measurement transmission line and the reference transmission line is substantially equal to a half wavelength of the lowest measuring frequency.

16. The sensor device of claim 1, wherein the measurement electrode and the reference electrode measure at least two parameters of the fluid mixture.

17. The sensor device of claim 16, wherein one measured parameter is an impedance measurement of the fluid mixture.

18. The sensor device of claim 1, wherein a portion of the electronics instrument package is positioned within a thermoelectric cooler, to maintain the portion of the electronics instrument package within a predetermined temperature range.

19. The sensor device of claim 1, wherein the electronics instrument package includes a means for detecting an anomaly in the measurement of the measured parameter and compensating the measurement for the detected anomaly.

20. The sensor device of claim 1, wherein the electronics instrument package includes a means for self-calibrating the sensor device to compensate for an anomaly detected in the measured parameter.

21. The sensor device of claim 1, wherein the electronics instrument package includes a voltage controlled oscillator, a reference oscillator, and a phase locked loop, wherein the phase locked loop matches the phase of the oscillation of the voltage controlled oscillator with the oscillation of the reference oscillator.

22. The sensor device of claim 21, wherein the reference oscillator is a crystal oscillator.

23. The sensor device of claim 1, wherein the electronics instrument package includes:
  a voltage controlled oscillator that is subject to loading;
  a means for frequently connecting a known load to the voltage controlled oscillator and detecting a variance in a response of the voltage controlled oscillator between connections to the known load; and
  a means for correcting the variance in the response of the voltage controlled oscillator.

24. The sensor device of claim 1, wherein the electronics instrument package includes:
  a voltage controlled oscillator having an original transfer function;
  a means for comparing a measured transfer function of the voltage controlled oscillator with the original transfer function to detect a variance in the original transfer function of the voltage controlled oscillator; and
  a means for correcting the variance in the original transfer function.

25. A sensor device for determining the concentration of fluid components comprising:
  a) a microcontroller;
  b) a probe including:
    (i) a body having slots for receiving a fluid mixture,
    (ii) a reference sensor within the body having a transmission line to the electronics instrument package, wherein the reference sensor has a reference electrode that is activated by the signal generating/receiving unit; and
    (iii) at least one measurement sensor within the body having a transmission line to the electronics instrument package, wherein the measurement sensor has a measurement electrode that is activated by the signal generating/receiving unit; and
  c) an electronics instrument package in communication with the microcontroller, the electronics instrument package having a signal generating/receiving unit in communication with the measurement transmission line and the reference transmission line, wherein the signal/receiving unit reciprocably activates the measurement electrode and the reference electrode to measure a parameter of the fluid mixture at a predetermined frequency, wherein the microcontroller calculates a permittivity of a component of the fluid mixture based on multiple measurements of the measured parameter by the reference sensor and the measurement sensor;
  whereby the microcontroller determines the concentration of the component in the fluid mixture using the calculated permittivity.

26. The sensor device of claim 25, wherein the fluid mixture creates a dielectric layer between the body of the sensor device and the measurement sensor.

27. The sensor device of claim 25, wherein the electrode in the reference sensor is isolated from the fluid mixture and wherein the electrode in the measurement sensor is exposed to the fluid mixture.

28. The sensor device of claim 25, wherein the sensor device further comprises a reference temperature detector imbedded in the sensor device and sealingly connected to the electronics package for monitoring a temperature and a pressure of the fluid mixture.

29. The sensor device of claim 25, wherein the generated signal has multiple frequencies to increase the accuracy of measurements for the individual components within the fluid mixture.

30. The sensor device of claim 25, further comprising two or more measurement sensors positioned in the sensor device to measure different properties of the fluid mixture.

31. The sensor device of claim 25, further comprising two or more measurement sensors differing by using various types of electrical load at the end.

32. The sensor device of claim 25, wherein the transmission lines to the reference sensor and the measurement sensor have a length equal to a multiple of a half wavelength of the lowest measuring frequency.

33. The sensor device of claim 25, wherein the transmission line to each reference sensor and each measurement sensor has an independently adjustable length.

34. The sensor device of claim 25, wherein the transmission lines to the reference sensor and the measurement sensor are substantially the same length.

35. A method for determining the concentration of fluid mixture components comprising the steps of:
  a) immersing a sensor device into a fluid mixture, wherein the sensor device comprises a microcontroller, a reference sensor and a measurement sensor mounted in a sensor housing, wherein the reference sensor and the measurement sensor include an electrode and a transmission line from a signal source, and an electronics instrument package in communication with the microcontroller, the electronics instrument package having a signal generating/receiving unit in communication with the measurement transmission line and the reference transmission line, wherein the signal/receiving unit reciprocably activates the measurement electrode and the reference electrode to measure a parameter of the fluid mixture at a predetermined frequency;

b) providing a substantially identical exposure of the reference and the measurement sensors to a pressure and a temperature of the fluid mixture;

c) making multiple, approximately concurrent measurements of a number of identified parameters by the measurement sensor electrode at various predetermined frequencies;

d) activating the reference sensor to detect anomalies in the measured parameters;

e) applying a compensation factor to the measured parameters to compensate for the detected anomalies;

f) calculating a permittivity of each component of the fluid mixture based on the compensated parameters; and g) using the calculated permittivities at the selected measurement frequencies to determine the concentration of each component in the fluid mixture.

36. The method of claim 35, wherein the immersing step further comprises the step of shielding the electrode of the reference sensor from the fluid mixture while exposing the electrode of the measurement sensor to the fluid mixture.

37. The method of claim 36, wherein the making measurements step further comprises the steps of:
a) identifying parameters to be measured;
b) energizing the measurement sensor electrode;
c) transmitting a signal at a known, constant frequency through a predetermined transmission line to the measurement sensor electrode;
d) measuring the signal sent to the measurement sensor electrode;
e) acquiring and measuring the reflected signal from the measurement sensor electrode;
f) repeating the energizing, transmitting, measuring and acquiring steps until at least two measurements for each identified parameter are made for the measurement sensor electrode at the known, constant frequency;
g) changing the transmission frequency at a predetermined rate; and
h) repeating the energizing, transmitting, measuring, acquiring, repeating and changing steps to produce a predetermined plurality of measurements at predetermined frequencies.

38. A method for determining the concentration of fluid mixture components comprising the steps of:
a) immersing a sensor device into a fluid mixture, wherein the sensor device comprises a microcontroller, a reference sensor and a measurement sensor, wherein the reference sensor and the measurement sensor include an electrode and a transmission line from a signal source, and an electronics instrument package in communication with the microcontroller, the electronics instrument package having a signal generating/receiving unit in communication with the measurement transmission line and the reference transmission line, wherein the signal/receiving unit reciprocably activates the measurement electrode and the reference electrode to measure a parameter of the fluid mixture at a predetermined frequency, wherein the electrode of the reference sensor is shielded from the fluid mixture whenever the electrode of the measurement sensor is exposed to the fluid mixture;

b) providing a substantially identical exposure of the reference and the measurement sensors to a pressure and a temperature of the fluid mixture;
c) identifying parameters to be measured;
d) energizing the measurement sensor electrode;
e) transmitting a signal at a known, constant frequency through a predetermined transmission line to the measurement sensor electrode;
f) measuring the signal sent to the measurement sensor electrode;
g) acquiring and measuring the reflected signal from the measurement sensor electrode;
h) repeating the energizing, transmitting, measuring and acquiring steps until at least two measurements for each identified parameter are made for the measurement sensor electrode at the known, constant frequency;
i) changing the transmission frequency at a predetermined rate;
j) repeating the energizing, transmitting, measuring, acquiring repeating and changing steps to produce multiple, approximately concurrent measurements of the identified parameters by the measurement sensor electrode at various predetermined frequencies;
k) activating the reference sensor to detect anomalies in the measured parameters;
l) applying a compensation factor to the measured parameters to compensate for the detected anomalies;
m) calculating a permittivity of each component of the fluid mixture .based on the compensated parameters; and
n) using the calculated permittivities at the selected measurement frequencies to determine the concentration of each component in the fluid mixture.

39. The method of claim 38, wherein the activating step further comprises the steps of:
a) using, at predetermined times during the process, the reference sensor to determine required compensation factors for the identified parameters; and
b) adjusting the identified parameters with the compensation factors.

40. The method of claim 38, further comprising the step of agitating the fluid mixture during the measurement step to provide a more representative mixture of the components of the fluid mixture.

41. The method of claim 38, wherein at least one phase-lock-loop-controlled oscillator circuit is coupled to the sensor device via a transmission line for automatically selecting the operating frequency to be transmitted, modifying the frequency as required to lock the frequency at the desired value and allowing rapid frequency changes and accurate frequency locks within a given frequency range.

42. The method of claim 41, further comprising the step of using multiple phase-lock-loop-controlled oscillator circuits to provide a broader range of frequency measurements during designated measurement periods.

43. The method of claim 41, wherein the identified parameters are the tuning/output voltage from the phase-lock-loop-controlled oscillator circuits when the frequency is locked, the forward voltage to the sensor and the reflected voltage from the sensor.

44. The method of claim 38, wherein the signal is a radio frequency signal.

45. The method of claim 38, wherein the signal is a microwave signal.

46. The method of claim 38, wherein the transmission lines are of substantially identical lengths.

47. A method for monitoring the concentration of individual components within a fluid mixture, comprising the following steps of:
   a) providing a sensor device comprising a microcontroller, a reference sensor and a measurement sensor mounted in a sensor housing, wherein the reference sensor and the measurement sensor include an electrode and a transmission line from a signal source, wherein the transmission lines are independently adjustable in length and an electronics instrument package in communication with the microcontroller, the electronics instrument package having a signal generating/receiving unit in communication with the measurement transmission line and the reference transmission line, wherein the signal/receiving unit reciprocably activates the measurement electrode and the reference electrode to measure a parameter of the fluid mixture at a predetermined frequency;
   b) exposing an electrode of at least one measurement sensor to the fluid mixture;
   c) shielding the reference sensor from the fluid mixture;
   d) providing identical exposure of at least one measurement sensor and the reference sensor to a pressure and a temperature of the fluid mixture;
   e) transmitting a signal to the reference sensor;
   f) receiving a reflected signal from the reference sensor;
   g) transmitting a signal to at least one measurement sensor;
   h) receiving a reflected signal from at least one measurement sensor;
   i) detecting the difference in the transmitted and reflected signals;
   j) using the detected differences to calculate the permittivities of the components of the fluid mixture;
   k) determining the concentration of individual components within the fluid mixture based on the calculated permittivities of the components; and
   l) repetitively sampling and processing the transmitted and reflected signals to produce a plurality of samples for real time monitoring of the concentration of individual components in the fluid mixture.

48. A sensor device for determining the concentration of fluid components within a fluid mixture comprising:
   a) a microcontroller;
   b) a sensor probe including:
      (i) a probe housing having a fluid passageway, such that when the probe housing is positioned in a fluid flow conduit a fluid mixture flowing through the flow conduit can pass through the fluid passageway in the probe housing,
      (ii) a reference sensor mounted within the probe housing, the reference sensor having a reference electrode in communication with a reference transmission line, wherein a portion of the reference electrode is covered by a reference isolator, and
      (iii) a measurement sensor mounted within the probe housing and coaxially offset from the reference sensor and the probe housing, the measurement sensor having a measurement electrode in communication with the fluid mixture and a measurement transmission line; and
   c) an electronics instrument package in communication with the microcontroller, the electronics instrument package having a signal generating/receiving unit in communication with the measurement transmission line and the reference transmission line, wherein the signal/receiving unit reciprocably activates the measurement electrode and the reference electrode to measure a predetermined parameter of the fluid mixture at a predetermined frequency, wherein the microcontroller calculates a compensation factor based on at least one measurement of the measured parameter by the reference sensor and a permittivity of a component of the fluid mixture based on multiple compensated measurements of the measured parameter by the measurement sensor;
   whereby the microcontroller determines the concentration of the component in the fluid mixture using the calculated permittivity.

49. A sensor device for determining the concentration of fluid components comprising:
   a) a microcontroller;
   b) an electronics package in communication with the microcontroller, wherein the electronics package has a signal generating/receiving unit, wherein the signal/generating unit includes a means for changing the generated signal at a predetermined rate, each generated signal selected from a set of predetermined signals; and
   c) a probe in communication with the electronics package, wherein the probe comprises:
      (i) a body having slots for receiving a fluid mixture,
      (ii) a reference sensor mounted within the body having a transmission line to the electronics instrument package, wherein the reference sensor has a reference electrode that is activated by the signal generating/receiving unit; and
      (iii) a measurement sensor mounted within the body axially offset from the probe body and the reference sensor, wherein the measurement sensor has a transmission line to the electronics instrument package and a measurement electrode activated by the signal generating/receiving unit to produce multiple measurements of selected parameters;
   d) wherein the signal/receiving unit reciprocably activates the measurement electrode and the reference electrode to measure a predetermined parameter of the fluid mixture at a predetermined frequency; and
   e) wherein the microcontroller compensates for anomalies in the measured parameters based on data acquired by the microcontroller from the reference sensor, calculates the permittivities of at least two individual fluid components based on the compensated measurements of the measurement sensor, and determines the concentration of the individual fluid components in the fluid mixture.

* * * * *